(12) United States Patent
Qian et al.

(10) Patent No.: US 9,490,109 B2
(45) Date of Patent: *Nov. 8, 2016

(54) GENERATION OF MODEL OF COMPOSITION OF PETROLEUM BY HIGH RESOLUTION MASS SPECTROMETRY AND ASSOCIATED ANALYTICS

(71) Applicant: ExxonMobil Research and Engineering Company, Annandale, NJ (US)

(72) Inventors: Kuangnan Qian, Skillman, NJ (US); Kathleen E Edwards, Freehold, NJ (US); Anthony S. Mennito, Flemington, NJ (US); Roland B. Saeger, Runnemede, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 16 days.

This patent is subject to a terminal disclaimer.

(21) Appl. No.: 14/178,627

(22) Filed: Feb. 12, 2014

(65) Prior Publication Data

US 2014/0231641 A1    Aug. 21, 2014

Related U.S. Application Data

(63) Continuation of application No. 13/167,816, filed on Jun. 24, 2011, now abandoned.

(60) Provisional application No. 61/423,797, filed on Dec. 16, 2010.

(51) Int. Cl.
*G01N 33/00*    (2006.01)
*H01J 49/00*    (2006.01)
*G01N 33/28*    (2006.01)

(52) U.S. Cl.
CPC ....... *H01J 49/0027* (2013.01); *G01N 33/2835* (2013.01)

(58) Field of Classification Search
None
See application file for complete search history.

(56) References Cited

U.S. PATENT DOCUMENTS 4,865,746 A    9/1989    Overfield
7,509,837 B2    3/2009    Lubkowitz et al.
2010/0230587 A1    9/2010    Marshall et al.

OTHER PUBLICATIONS

Qian, K. et al. Observation of vanadyl porphyrins and sulfurcontaining vanadyl porphyrins in a petroleum asphaltene by atmospheric pressure photonionization Fourier transform ion cyclotron resonance mass spectrometry, 2008, Rapid Communications in Mass Spectrometry, vol. 22, pp. 2153-2160.*
Fiehn, Mass Resolution and Resolving Power—Metabolomics Fiehn Lab, retrieved from internet: http://web.archive.org/web/20091001044045/http://fiehnlab.ucdavis.edu/projects/Seven_Golden_Rules/Mass_Resolution/.*

(Continued)

*Primary Examiner* — Robert Xu
(74) *Attorney, Agent, or Firm* — Ronald D. Hantman; Andrew T. Ward; Glenn T. Barrett

(57) ABSTRACT

A method to determine the model-of-composition of a vacuum resid in which the resid is separated into fractions including the DAO fraction which is then separated into chemical classes including saturates, aromatics, sulfides and polars by a combination of soft ionization methods. The results of the ionization analysis are reconciled with other analysis such as bulk analysis, then consolidated to generate the modeol-of composition.

11 Claims, 16 Drawing Sheets

(56) References Cited

OTHER PUBLICATIONS

Miyabashi et al., "Constituent Analysis of DAO before and after Hydrocracking over Zeolite Catalyst by Ultra-high Resolution Fourier Transform Ion Cyclotrol Resonance Mass Spectrometry", XP-002673940, Proceedings of 15th Saudi-Japan Joint Symposium, Dhahran, Saudi Arabil, Nov. 27-28, 2005, pp. 1-10.

Barman et al., "Petroleum and Coal", XP-002673941, Analytical Chemistry (2001), vol. 73, pp. 2791-2804.

Al-Hajji et al., "Characterization of Nitrogen and Sulfur Compounds in Hydrocracking Feedstocks by Fourier Transform Ion Cyclotron Mass Spectrometry", XP-002673942, Oil & Gas Science and Technology—Rev. IFP, vol. 63, (2008), No. 1, pp. 115-128.

\* cited by examiner

*On-line HPLC FTICR MS Configuration*

GENERATION OF MODEL OF COMPOSITION OF PETROLEUM BY HIGH RESOLUTION MASS SPECTROMETRY AND ASSOCIATED ANALYTICS

This application is a continuation of application Ser. No. 13/167,816, filed 24 Jun. 2011 which, in turn, was a Non-Provisional application based on Provisional Application 61/423,797 filed Dec. 16, 2010. This application claims priority under 35 USC 120 from application Ser. Nos. 13/167,816 and 61/423,797.

BACKGROUND OF THE INVENTION

The present invention is a method to determine a model-of-composition for petroleum and petroleum related products. In particular the petroleum is a vacuum resid (VR) or vacuum gas oil (VGO) or petroleum with a similar boiling point range.

A vacuum gas oil is a crude oil fraction that boils between about 343° C. to 537° C. A vacuum residuum is a residuum obtained by vacuum distillation of a crude oil and boils above a temperature about 537° C.

Petroleum samples are complicated hydrocarbon mixtures containing paraffins, cyclic paraffins, multiring aromatics, and various heteroatomic hydrocarbons (most commonly O, S, and N). Virgin petroleum crude oils contain molecules of a wide boiling point range from highly volatile $C_4$ hydrocarbons to nonvolatile asphaltenes. Analysis of petroleum composition of various boiling ranges is necessary for inputs to many subsequent processes.

SUMMARY OF THE INVENTION

Petroleum streams are complex mixtures of hydrocarbons containing enormous numbers of distinct molecular species. These streams include any hydrocarbon stream from processes that change petroleum's molecular composition. The streams are so complex, and have so many distinct molecular species that any molecular approximation of the composition is essentially a model, that is, a model-of-composition (MoC).

Petroleum oils and high-boiling petroleum oil fractions are composed of many members of a relatively few homologous series of hydrocarbons (6). The composition of the total mixture, in terms of elementary composition, does not vary a great deal, but small differences in composition can greatly affect the physical properties and the processing required to produce salable products. Petroleum is essentially a mixture of hydrocarbons, and even the non-hydrocarbon elements are generally present as components of complex molecules predominantly hydrocarbon in character, but containing small quantities of oxygen, sulfur, nitrogen, vanadium, nickel, and chromium. Therefore, in the present invention petroleum and hydrocarbon will be used interchangeably.

The present invention is a method to determine the model-of-composition of a heavy petroleum or hydrocarbon sample. The method includes the steps of obtaining molecular ions or pseudo molecular ions of the sample by soft ionization, determining molecular ion formulas and quantifying corresponding concentrations and then reconciling this quantification with other analytical measurements to obtain a model-of-composition.

In a preferred embodiment, one or multiple soft ionization methods are used to generate molecular ions or pseudo molecular ions for petroleum molecules of different polarities and classes.

Pseudo molecular ions include protonated ions, deprotonated ions, cation or anion adduct of parent molecule of the heavy petroleum or hydrocarbon sample.

In a preferred embodiment, elemental formulas and concentrations of molecular ions or pseudo molecular ions are determined by high resolution mass spectrometry In a preferred embodiment, the petroleum are separated into asphaltenes and deasphalted oils (DAO) before mass spectrometric analysis. A deasphalted oil remains after the asphaltene fraction is removed by the addition of a low boiling hydrocarbon liquid such as n-pentane or n-heptane.

In a preferred embodiment, the DAO are separated into saturates, aromatics, sulfides, and polars before mass spectrometric analysis.

In a preferred embodiment, aromatics are separated into aromatic ring classes (ARC), 1—Ring Aromatics (ARC1), 2—Ring Aromatics (ARC2), 3—Ring Aromatics (ARC3), and 4—Ring Aromatics Plus (ARC4+) before mass spectrometric analysis.

In another embodiment, the petroleums are separated and analyzed by on-line separation mass spectrometry.

In a preferred embodiment, the petroleum sample is a vacuum resid or a sample that boils above about 1000° F.

In another embodiment, the petroleum sample is a vacuum gas oil or a sample that boils between about 650° F. to 1000° F.

DESCRIPTION OF THE PREFERRED EMBODIMENT

Figure 1:
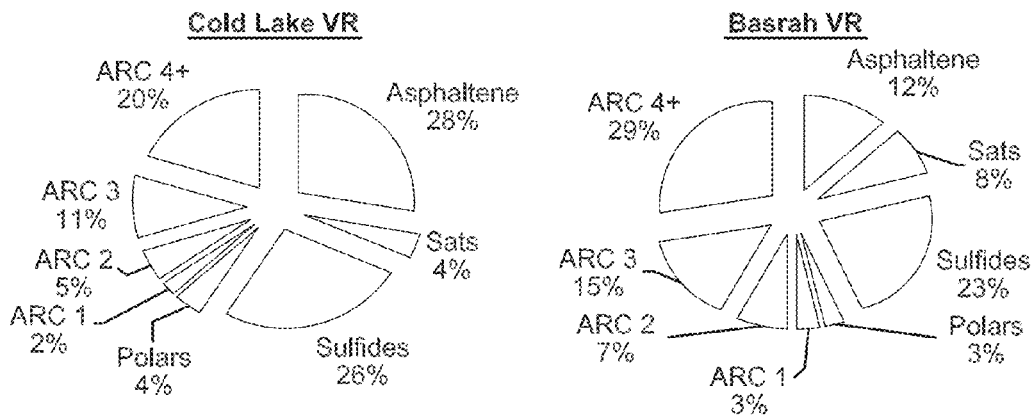
FIG. 1 shows the separation of two vacuum resids into eight composition lumps.

The present invention is a method to generate a model-of-composition for petroleum and petroleum related products using high resolution mass spectrometry and associated analytical techniques.

Petroleum samples are analyzed by high resolution mass spectrometry (HRMS) to resolve or partially resolve nominal mass overlap in the samples. Mass resolution here is defined as $R=M/\Delta M_{FWHM}$ where $/\Delta M_{FWHM}$ is defined as mass peak width at 50% peak height. Mass resolving power (RP) and mass resolution are used interchangeably in this work. A minimum of 10,000 mass resolution is needed to resolve important overlaps including 12H~C doublet as listed in Table 1. In this work, data are collected in a broadband acquisition mode (a mass range of 100 to 3000 Da). Preferably, Fourier transform ion cyclotron resonance mass spectrometry (FTICR-MS) with an average mass resolving power (RP>300K) is utilized for the analysis. Samples may be analyzed directly or after separation by off-line or on-line chromatography, or solubility fractionation. Petroleum samples or fractions are ionized by one or combined soft ionization methods to generate molecular ions or pseudo-molecular ions that are representing different classes of petroleum molecules. Empirical formula can be determined without ambiguity within the accuracy of mass analysis window and restrictions of heteroatom combinations. Chromatographic separation may be used to generate petroleum lumps with different aromatic ring structures and/or chemical moieties. The separation also enhances dynamic range of the HRMS analysis. Molecular structure assignments are made based on empirical formula and aromatic ring classes. Quantitations are made by normalizing total components to the HPLC lumps. At the end, composition may be reconciled so that average composition and properties are consistent with that measured by bulk measurement technologies, such as NMR and elemental analysis.

In the past, a magnetic sector mass spectrometer was commonly used to determine petroleum composition. For example, MS50 has been the workhorse in the High Detail Hydrocarbon Analysis (HDHA) protocol. In general, a sector MS provides limited mass resolution. 10K to 50K can be normally achieved when used electron ionization (EI) mode and 1K to 5K when used in Field Ionization (FI) mode. More recently time of flight (TOF) mass spectrometer with RP around 5K has been used to determine petroleum compositions. EI produce too much fragmentation during the ionization process and cannot be used to determine molecular ion composition. The low mass resolution in FI mode prohibits resolutions of many overlapping masses in petroleum. Consequently, it is hard to make unique assignments of molecular formula for the molecular ions. Chromatographic (HPLC or GC) separations are necessary to assist mass spectrometry characterization. Although successful applications have been demonstrated and applied to petroleum analysis, the upper boiling point limit of these analytical protocols are typically below 1000° F. (VGO or below). Even in this boiling range, there are still many ambiguities in formula and structure assignments. There is no method for petroleum that boils above 1000° F. The technology described here filled the gap in petroleum vacuum resid characterization. With FTICR-MS and use of multiple ionization methods, we are able to develop a model-of-composition for petroleum vacuum resid.

The overall method is to use a combination soft ionization methods to generate molecular ions or pseudo molecular ions for petroleum molecules of different polarities and classes. Pseudo molecular ions are defined as protonated or deprotonated molecular ions, cation or anion adducts of molecular ions. FTICR-MS resolves and determines masses with high accuracy (error<0.2 ppm). Concentrations of the masses are determined by the signal magnitude of corresponding masses. Empirical formulas were assigned based on the accurate masses and restrictions of heteroatom combinations. Chromatographic separations may be used to increase dynamic range, assist quantification and structure assignments. Reconciliation may be conducted to match the average composition with that determined via bulk measurements.

The following is a typical work process to generate a model-of-composition for petroleum using high resolution mass spectrometry
1. Separations of petroleum molecules into like species or molecular lumps, such as
   a. Deasphalted oil (DAO) and asphaltenes
   b. Saturates, aromatics, sulfides and polars
   c. Aromatic ring classes
2. Generation of molecular ions or pseudo molecular ions
   a. Use of field desorption/field ionization to ionize saturate molecules
   b. Use of APPI/APCI to ionize aromatic petroleum molecules.
   c. Use of positive ion ESI (PEST) to ionize basic nitrogen molecules
   d. Use of negative ion ESI (NEST) to ionize acidic molecules
   e. Use of laser desorption ionization or matrix assisted laser desorption to ionize high boiling molecules (molecules boils above 1300 F).
3. Determination of compound class, Z distribution, carbon number distribution and stoichiometry of molecules by FTICR-MS
   a. Resolve all mass peaks
   b. Accurate mass analysis of molecular ions or pseudo molecular ions by conducting external and internal calibration
   c. Assign molecular formulas to the masses above a defined signal to noise threshold using a mass tolerance of 0.6 mDa.
      Only C, H, N, S, O, Ni and V are allowed. Maximum number of N, S, O are limited to 4. Maximum number of Ni and V are limited to 1.

d. Determine abundances of molecules based on FTICR-MS signal magnitude of the corresponding molecule ions or pseudo molecule ions
e. Group molecules and their abundances by heteroatom contents, homologous series (Z-number) and molecular weights
4. Assemble full composition by combining compositions from various molecular lumps and ionization methods
5. Reconcile with other analytical data, such as
   a. Field Desorption MS for Molecular Weight (MW) distribution
   b. Bulk Properties
      i. Elementals
      ii. High temperature simulated distillation (HT-SIM-DIS)
      iii. Microcarbon residue (MCR) or conradison carbon (CCR) Residue
   c. Average structures by NMR
      i. % Aromatic carbon (Ca)
      ii. Average aromatic cluster size (C#)
      iii. Amount of C in long chains
      iv. Degree of chain branching
   d. Heteroatom types by X-ray Photoelectron Spectroscopy (XPS)
      i. Organic forms of sulfur
      ii. Pyrrolic, pyridinic and quaternary nitrogens Separations of Petroleum Molecules into Like Species Although petroleum samples can be analyzed directly by FTICR-MS to generate a composition, separation of petroleums into like species helps to improve dynamic range of mass analysis, facilitate quantitation and structural assignments. For vacuum resid, deasphalt is normally the first step before further chromatographic separation. HPLC can separate petroleum into saturates, aromatics, sulfides and polars. Aromatics may be further divided into ring classes. FIG. 1 shows the separation of two vacuum resid into eight composition lumps. Deasphalt and HPLC separations can be performed off-line or on-line with FTICR-MS.

Generation of Molecular Ions or Pseudo Molecular Ions

Soft ionization methods are used to generate molecular ions or pseudo molecular ions. Commonly used ionization methods include but not limited to Electrospray Ionization (ESI), Atmospheric Pressure Chemical Ionization (APCI), Atmospheric Pressure Photoionization (APPI), Matrix Assisted Laser Desorption Ionization (MALDI) and direct laser ionization (LDI). Ionizations can be operated in both positive and negative ion mode. Among those ionization techniques, APPI and ESI were found to be most useful and are extensively explored in this work. APPI ionizes both aromatic and polar aromatic molecules mostly via charge transfer reactions (minor protonations have also been observed). However, it does not ionize saturate structures (especially paraffinic structures) due to high ionization potentials of analyte molecules. Saturate molecules can be ionized by field desorption or field ionization. APCI produces similar products as in APPI. MALDI and LDI can ionize high molecular weight and high boiling molecules (e.g. 704° C.+). Compositions from various ionization methods can be combined.

Figure 2:
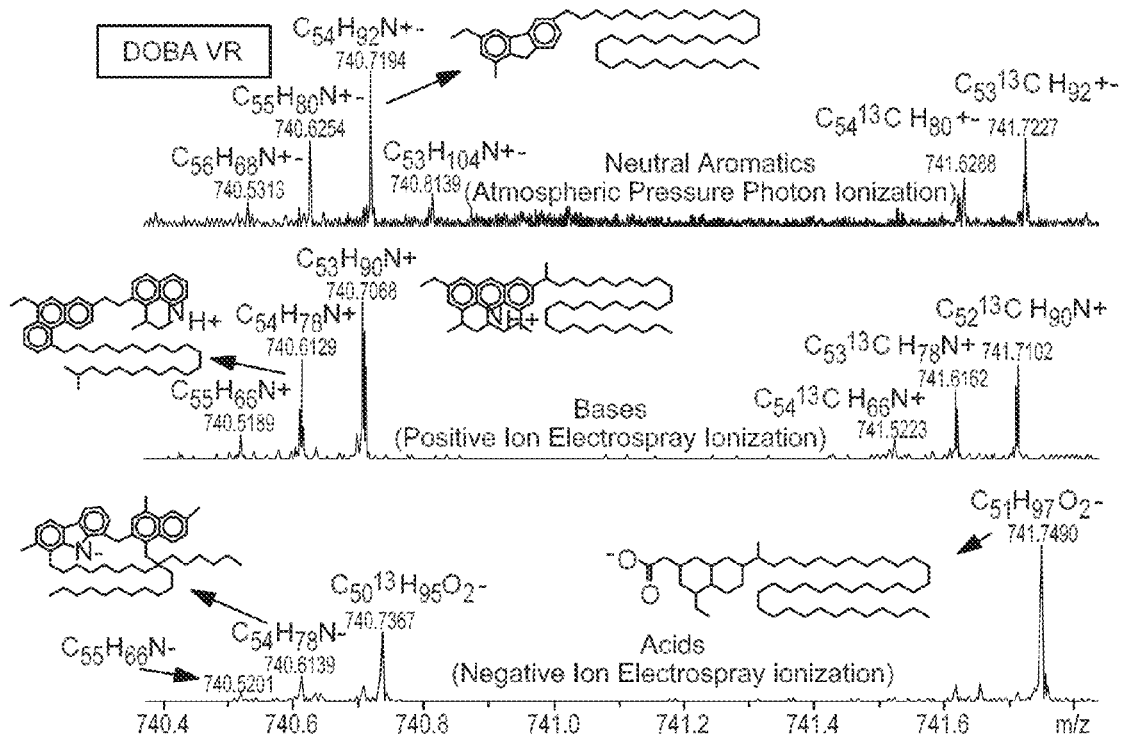
FIG. 2 shows the use of multiple ionization methods to generate molecular ions or pseudo molecular ions of different petroleum classes. Analyses were done without chromatographic separations.
Figure 3:
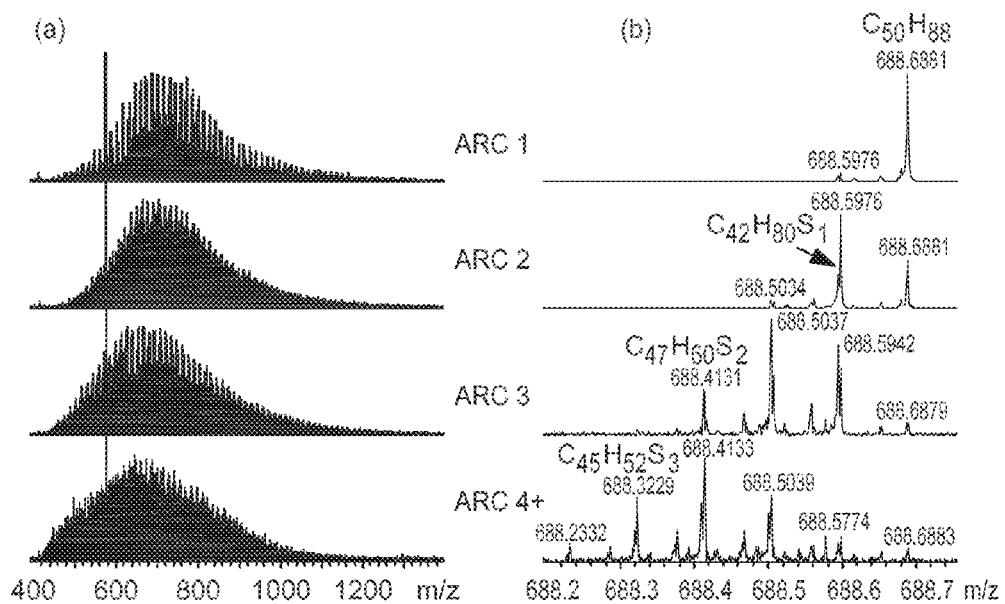
FIG. 3 shows the ionization of aromatic ring classes by Atmospheric Pressure Photoionization (APPI) for Cold Lake VR ARC fractions (a) full range (b) M/Z of 688.
Figure 4:
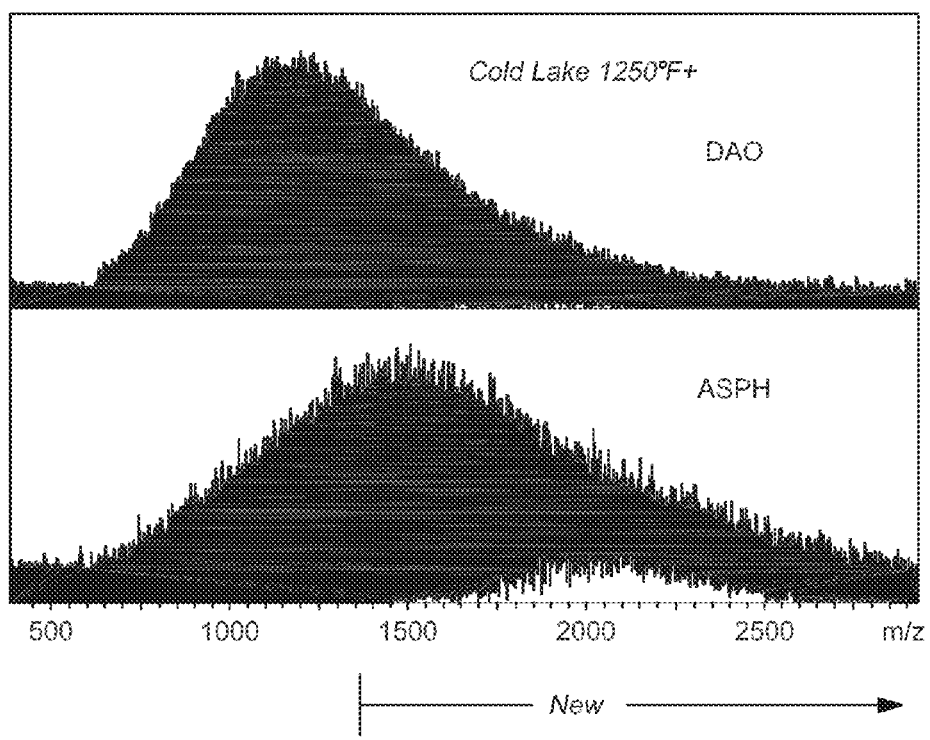
FIG. 4 shows the ionization of 1250° F.+ molecules asphaltenes and deasphalted oil (DAO) by laser desorption. Molecular weight species beyond 1500 g/mol are new species that cannot be volatized by APPI.
Figure 5:
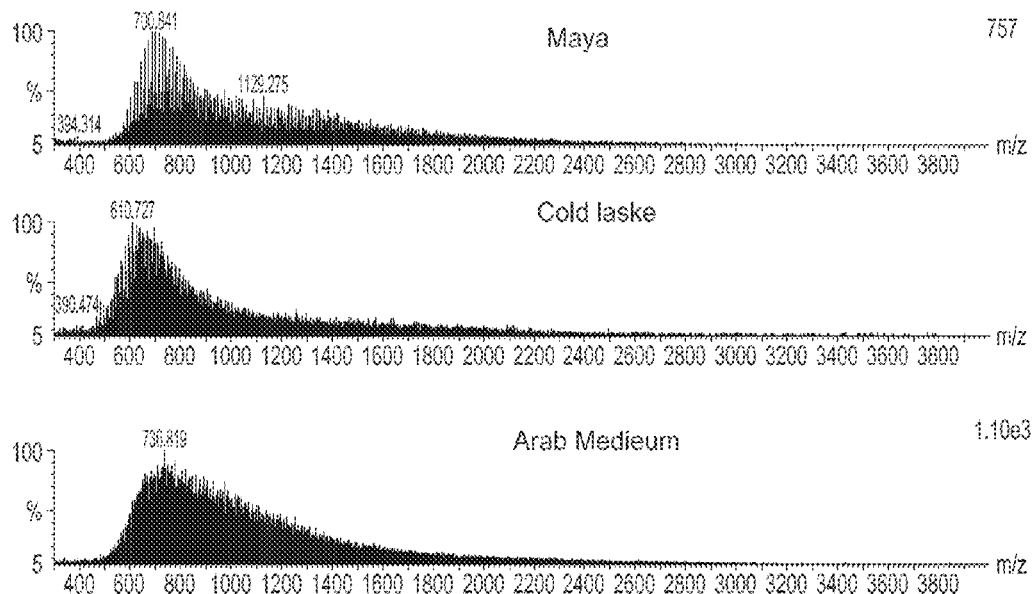
FIG. 5 shows the ionization of saturate molecules by field desorption.
Figure 6:
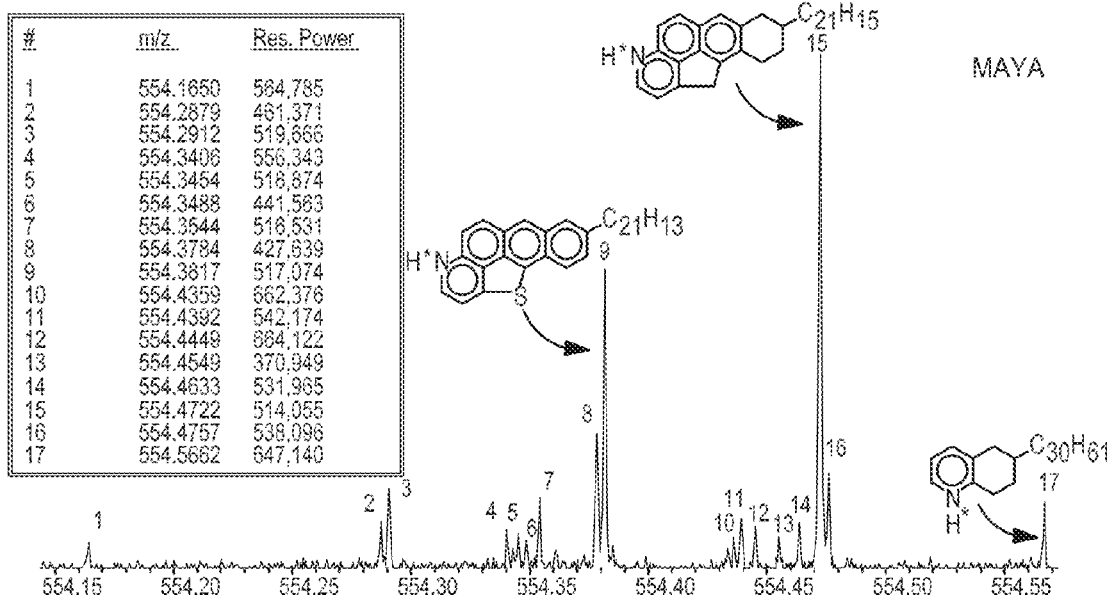
FIG. 6 shows the ultra-high mass resolving power by Fourier transform ion cyclotron resonance mass spectrometry (FTICR-MS) needed to resolve petroleum molecules.
Figure 7:
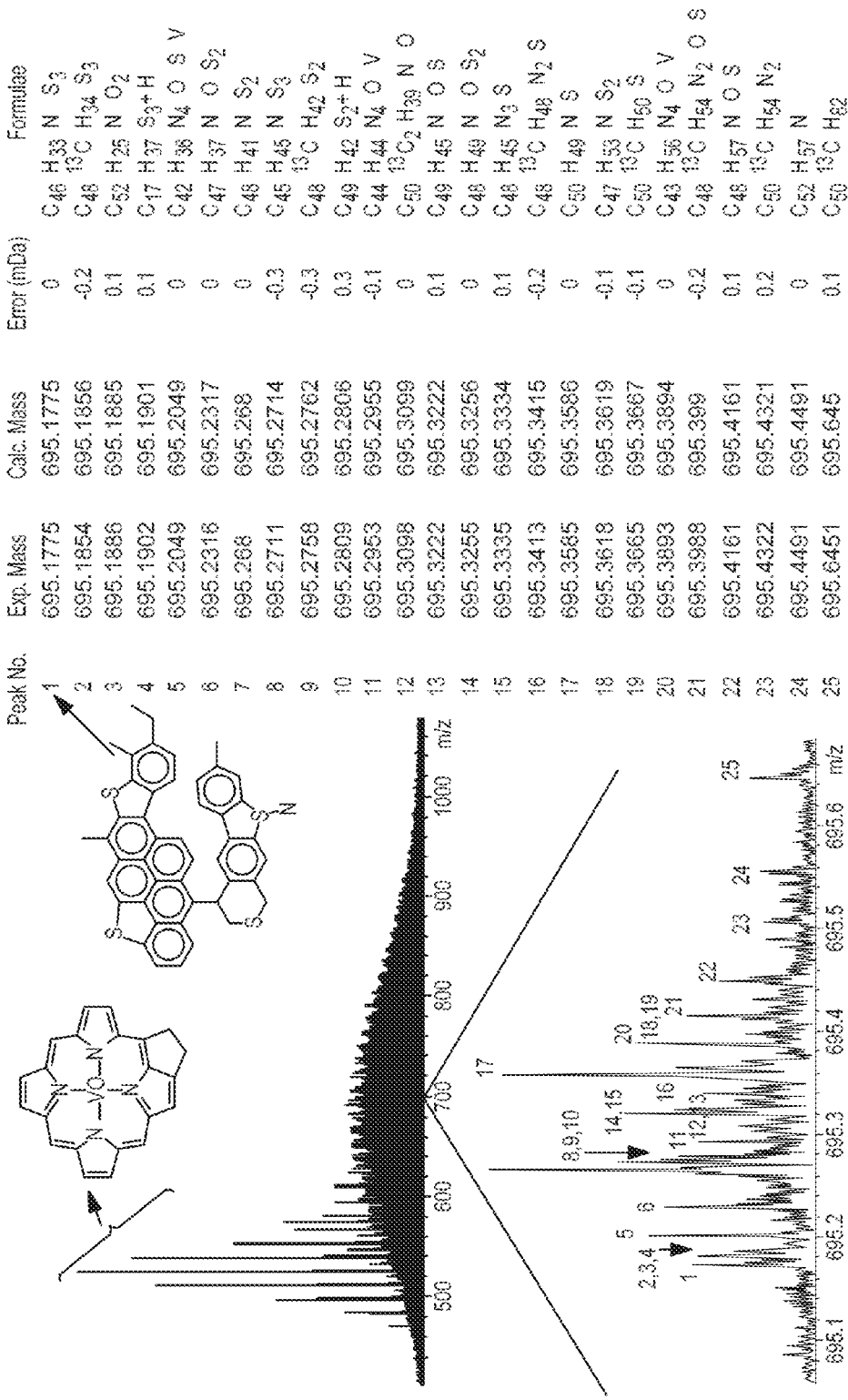
FIG. 7 shows the assignments of molecular formulas for an asphaltene sample.

FIG. 2 shows the use of multiple ionization method to generate molecular ions for neutrals, bases and acids by APPI, PESI and NESI, respectively. FIG. 3 shows the ionization of aromatic ring classes by APPI. FIG. 4 shows ionization of 677° C.+ molecules by laser desorption ionization mass spectrometry. FIG. 5 shows ionization of saturate molecules by field desorption ionization Determine Compound Classes, Z Distribution, Total Carbon Number Distribution and Stoichiometry of Molecules by FTICR-MS FTICR-MS provides accurate mass analysis of petroleum of a wide molecular weight range. Internal calibration using sample peaks are normally performed. Mass accuracy of 0.2 ppm can be achieved after internal calibration. An average mass resolving power greater than 300,000 is necessary to resolve petroleum molecules. FIG. 6 demonstrated ultra-high mass resolving power (>500,000) over a wide mass range (200-1200 Da) achieved by FTICR-MS. FIG. 7 shows assignments of molecular formula for an asphaltene samples with error less than 0.2 mDa.

Figure 8:
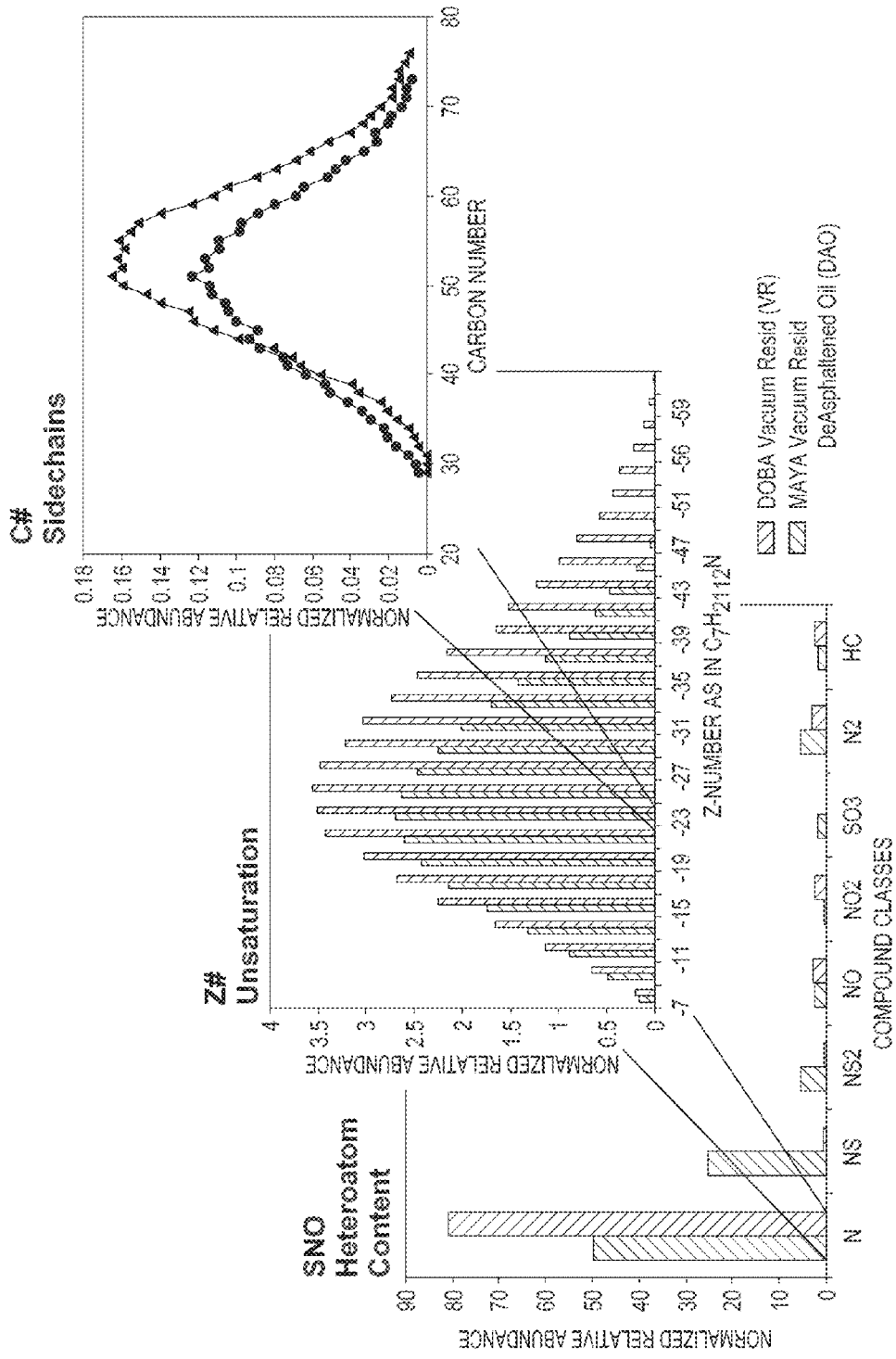
FIG. 8 shows the layers of chemical information provided by FT ICR-MS.

FTICR MS provides three layers of chemical information for a petroleum system as shown in FIG. 8. The first level is heteroatomic classes (or compound classes), such as hydrocarbons (HC), 1 sulfur molecules (1S), 1 nitrogen molecules (1N), 2 oxygen molecules (2O), 1 nitrogen 1 oxygen molecules (1N1O), etc. The second level is Z-number distribution (or homologous series distribution) within each compound class. Z is defined as hydrogen deficiency as in general chemical formula, $CH_{2c+z}N_nS_sO_o$. The more negative the Z-number, the more unsaturated the molecules. The third level of information is the total carbon number distribution or molecular weight distribution of each homologue. If compound core structure is known, total alkyl sidechain information can be derived by subtracting carbon number of cores.

Assemble-Full Composition by Combining Compositions from Various Molecular Lumps and Ionization Methods Molecular composition of petroleum is too complex to be determined adequately by a single FTICR MS analysis. Instead, a petroleum sample is subjected to an advanced analytical protocol that includes multiple steps and analyses (see schematic in FIG. 9). If the sample's initial boiling point is at or above 1000° F., asphaltenes are separated from the sample first. The deasphalted oil (DAO), is further separated using a high-performance liquid-chromatographic (HPLC) technique. The fractions that elute from this HPLC technique include: saturates, aromatic-ring classes (ARC) 1-4, sulfides, and polars. Each of these fractions, including asphaltenes, are analyzed by a variety of techniques, including: FTICR MS, field-desorption mass spectrometry (FDMS), nuclear magnetic resonance (NMR), elemental analysis, and other bulk properties, APPI FTICR MS is used to estimate the distribution of chemical formulae within the ARC 1-4, sulfides, and asphaltene fractions. The molecular composition of the polar fraction is known to be dominated by molecules containing basic nitrogen, and containing organic acid groups. Here, the distribution of chemical formulae is estimated by analyzing the DAO by NESI (negative ion ESI) FTICR MS, and by PESI (positive ion ESI) FTICR MS, then superimposing the two analyses.

Reconcile/Leverage with Other Analyticals

Figure 9:
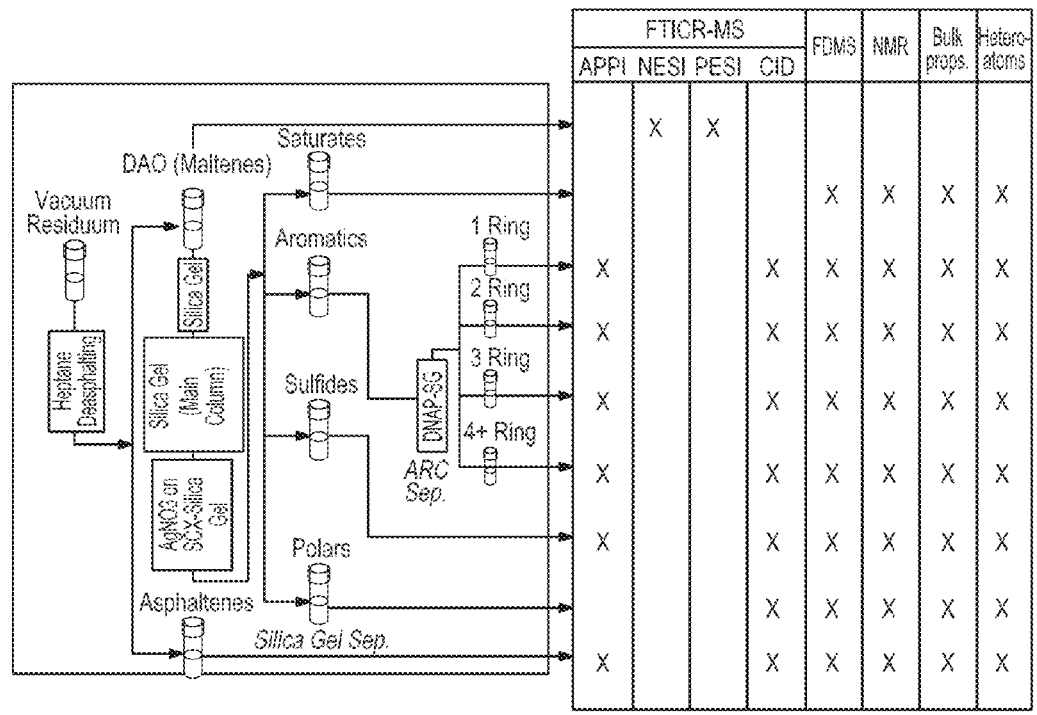
FIG. 9 shows the reconciliation of the chemical distribution with the advanced analytical protocol.

The chemical formulae distribution determined by FTICR MS analysis of the separated fractions detailed above must be reconciled to all analyses within the advanced analytical protocol shown in FIG. 9. Each fraction's FTICR MS analysis must be extrapolated to higher molecular weights, and lower hydrogen deficiency classes (Z-number), to match the molecular weight distribution predicted by FDMS analysis. The total abundance of elements in each fraction, e.g. carbon, hydrogen, sulfur, nitrogen, oxygen, nickel, and vanadium, as predicted from the FTICR MS-derived chemical formulae must be reconciled to that measured by elemental analysis. This reconciliation is done using the constrained entropy maximization procedure. Reconciliation to high-temperature is feasible through use of appropriate property targets in the above procedure, and through the use of a correlation that relates boiling point temperatures to chemical formulae. Assignment of molecular (e.g. structure oriented lumping (SOL)) lumps to each chemical formula is aided by other measured properties, e.g. microcarbon residue, NMR, and heteroatom types identified by X-ray Photoelectron Spectroscopy (XPS).

Appendix I provides more details on the determination of heavy petroleum composition using multiple ionization methods and Fourier transform ion cyclotron resonance mass spectrometry.

Appendix II provides more details on the molecular formula distributions of vacuum resid reconciled to the heavy hydrocarbon model-of-composition analytic protocol.

APPENDIX I

Determination of Heavy Petroleum Composition Using Multiple Ionization Methods and Fourier Transform Ion Cyclotron Resonance Mass Spectrometry Introduction The primary goal of this research is to establish the next generation mass spectrometry platform for molecular characterization of heavy hydrocarbons with boiling points greater than 1000° F. These hydrocarbon molecules are often referred as the "bottoms of the barrel" as they cannot distill via conventional vacuum distillation tower. A more common name of this non-distillable fraction is called vacuum residua or vacuum resid (VR). Relative to a vacuum gas oils (VGO), VR exhibits very different chemical and physical characteristics. They present much higher analytical challenges, especially in the area of molecular level characterization. The first challenge is their high boiling points and high molecular weights. Nominally, the boiling points of VR molecules are above 1000° F. and molecular weights range from 300 Da to 2000 Da (versus 100 to 800 Da of VGO). The high molecular weights of VR arise from both alkyl chain extension ($CH_2$ increments) and poly aromatic ring growth. Traditional thermal vaporization and ionization methods are inefficient to convert VR molecules into intact molecular ions for detection. The second challenge is their low solubility. VR typically contain asphaltenes (defined as n-heptane insolubles in this work). The range of asphaltenes content is from 0 to 40%. The low solubility and high asphaltenes contents are largely arising from its rich heteroatom content (NSO) and low H/C ratio. The third challenge is the huge number of molecules in VR (50 to 100 times more than that in VGO in terms of mass distinguishable species) and significant increases in NSO and metal contributions. Mass spectrometry performance needs to be maximized in terms of mass resolution, mass accuracy and dynamic range to account for all molecules in VR. Finally, VR molecules are likely to contain multi-core structures (versus mostly single cores in VGO), making structure assignment difficult.

Mass spectrometric characterization of hydrocarbons has been the subject of research for over the past six decades. In the past, a sector mass spectrometer has been the major work horse for providing molecular information. In general, a sector MS provides a dynamic resolution (at mass of 100 Da) ranging from 10K to 50K when combined with electron ionization technology and 1K to 5K when used in Field Ionization (FI) mode. Its resolution decreases rapidly as molecular weight increases. FTICR-MS provides a quantum leap in the mass resolution and mass accuracy. For example, a 12 tesla FTICR-MS can easily obtain a mass resolution of 350K at a mass of 500 Da. Its mass accuracy can tell the mass difference of one electron (0.54 mDa). This capability enables resolution of almost all hydrocarbon nominal mass overlaps (Table 1) across entire mass range of interests. As stated before, the primary challenge in FTICR-MS applications for heavy petroleum characterization are the effective volatization and ionization of the high boiling and low solubility molecules. In addition, effective and non-bias transmission of ions from the ion source into the FTICR cell is also critical to the quantification aspect of the technique.

The overall strategy of our characterization is to leverage chromatographic separations to improve FTICR-MS in terms of dynamic range, quantification and structure assignments. This report will discuss APPI ionization of model compounds, aromatic ring class fractions, sulfides and asphaltenes. We will also discuss ESI ionization of polar molecules.

EXPERIMENTAL

Instruments

Bruker APEX-Qe is a hybrid quadrupole-FTICR MS with a 12 tesla actively shielded superconducting magnet. The instrument combines the power of ultra-high resolution FTICR with a linear hexapole-quadrupole-hexapole (hQh) ion trap technology. The hQh ion trap serves multiple purposes. First it allows efficient cooling and homogenization of ion kinetic energy (in the 1st hexapole) so that the ions entering ICR cell have similar linear velocity which is very critical for ultra-high resolution and ultra-high accuracy mass measurements. Secondly, ions can be purified or concentrated by the quadrupole mass analyzer for subsequent fragmentation (in the second hexapole) and ultra-high resolution analysis (in the FTICR cell). The fragmentation capability enables determination of heavy petroleum multi-core structures.

APPI Conditions and Sample Preparations

About 4 mg of petroleum sample are dissolved in 20 ml of toluene to form a 200 ppm solution. The solution was introduced into the APPI source using a Cole-Palmer syringe pump and a 250 µl syringe. The flow rate is normally controlled at 120 µl/hour. The source was manufactured by Syagen and comprised of a heated capillary needle and Krypton UV lamp with ionization energy of 10.6 eV. Nitrogen is used for both nebulizing gas and drying gas. Nebulizing gas flow rate is normally between 1 to 3 L/min while drying gas flow rate is normally between 2 to 7 L/min. The flow rates are adjusted to maximize APPI-FTICR signals. Nebulizing gas temperature varies from 350° C. to 450° C. For VR, 450° C. has been generally adopted to maximize the signal of high boiling molecules. Toluene is used as both solvent and chemical ionization agent. We did not observe any thermal chemistry in APPI. This is mainly due to the short residence time of the sample ions.

ESI Conditions and Sample Preparations

Optimal sample concentrations depend on nitrogen and acid levels. In positive ion ESI, ~20 mg of VR sample is first dissolved in 20 ml toluene. 3 ml of the solution is diluted with 17 ml of a toluene/ACN mixture (15% toluene). The final analyte concentration is about 150 ppm. The final toluene concentration is about 30%. 20 to 100 ul of formic acid was added to the solution to promote liquid conductivity. The desired electrospray current is greater than 10 uA to maintain spray stability. In negative ion mode, ~20 mg of VR sample is first dissolved in 20 ml toluene. 3 ml of the solution is diluted with 17 ml of toluene/methanol mixture (15% toluene). The final sample concentration is 150 ppm. 20 to 100 ul of NH4OH is added to promote liquid conductivity and achieve desired electrospray current of >10 uA. The liquid sample is delivered into ESI source by a syringe pump with a flow rate of 120 ul/hour. Nitrogen is used for both nebulizing and dryer gases. The nebulizing temperature is at ambient and the drying gas temperature is set at 200° C.

Samples

Samples analyzed in this report are derived from a series of deasphalt and HPLC separations. Deasphalt process has been previously described[1], which divides VR into asphaltenes and deasphalted oils (DAO). HPLC separation further divides DAO into aromatic ring classes (1 to 3 ring and 4-ring+), sulfides and polars[2,3].

Data Analysis and Integration

In FTICR MS, the excited cyclotron motion of the ions is detected on receiver plates as a time domain signal that contains all the cyclotron frequencies that have been excited. Fourier transformation of the time domain signal results in the frequency domain signal that can be converted into a mass spectrum. In this work, the mass range was set at m/z 300 to 3000. The dataset size is set to 4 Megawords. Ion accumulation time is 0.5 to 2 sec. 1000 data sets were co-added to generate the final spectrum. Bruker Data Analysis (DA) software is used to find the mass peak list with signal-to-noise ratio (S/N) greater than 6. The mass peak list is further analyzed for identification of hydrocarbon molecules. External mass calibration was performed using a blend of eight in-house synthesized aromatic compounds covering a mass range from ~350 to 1800 Da. In general, 2 ppm mass accuracy can be achieved with external calibration. Bruker DA molecular formula tool assisted in identifying major homologous series. Internal calibration was then performed using the identified homologous series. On average, ~0.2 ppm mass accuracy can be achieved with internal mass calibration.

Mass peak list containing columns of exact masses, signal magnitudes, mass resolving powers and signal-to-noise ratios were further processed to generate elemental formula $(C_cH_{2c+z}N_nS_sO_o)$. Data are organized into heteroatom classes and homologous series.

Results and Discussions

Soft Ionizations of Heavy Petroleum Molecules

Apex-Qe FTICR MS is equipped with multiple ionization techniques, Electrospray Ionization (ESI), Atmospheric Pressure Chemical Ionization (APCI), Atmospheric Pressure Photoionization (APPI) and Matrix Assisted Laser Desorption Ionization (MALDI). Among those ionization techniques, APPI and ESI were found to be most useful and are extensively explored in this work. APPI ionizes both aromatic and polar aromatic molecules mostly via charge transfer reactions (minor protonations have also been observed). However, it does not ionize saturate structures due to their high ionization potentials. ESI has been extensively explored for polar characterization. APCI produces more complex ionization products for petroleum (including extensive protonation and charge transfer). MALDI and Laser Desorption Ionization (LDI) have shown potential for ionizing high molecular weight polymers, asphaltenes and waxes.

Ionization of Aromatic Molecules by APPI

Figure 10:
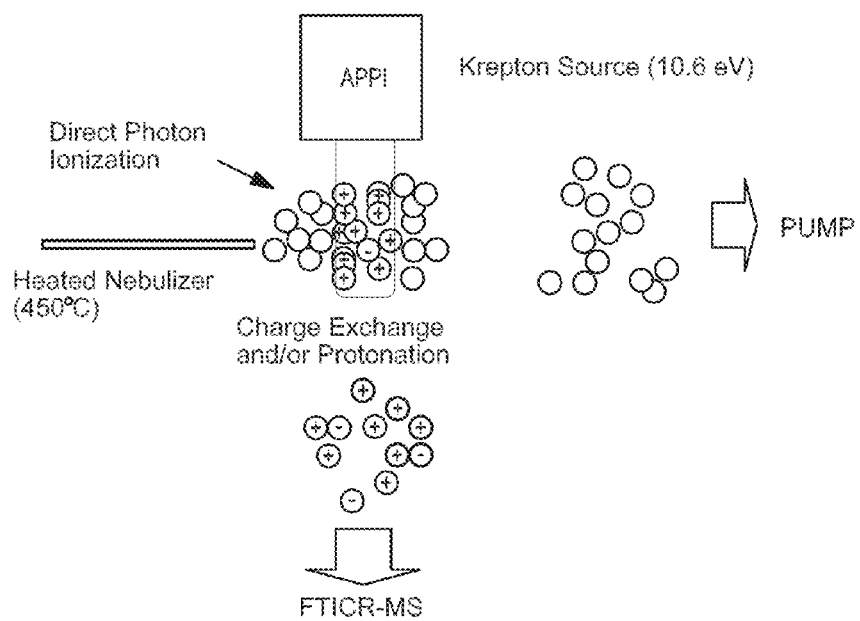
FIG. 10 shows APPI ionizations.

FIG. 10 demonstrates the basic principles of APPI. The sample solution is dispersed into fine droplets and vaporized by co-spraying with a nebulizing gas through a heated stainless needle. The sample molecules are further desolvated by a counter flow of drying gas. The gas phase solvent and analyte molecules are ionized via UV photoionization. Since analyte molecules are present in a much lower level (200 ppm), the gas phase contains primarily solvent molecules. Consequently, direct photoionization produces mostly solvent molecule ions and very few analyte ions. The latter are mostly ionized by secondary ion-molecule reactions in the source region. In the current applications, toluene is used as solvent as it can dissolve most of the sample types including asphaltenes. Toluene has an ionization potential (IP) of 8.8 eV and can be directly ionized by Krypton photon source (10.6 eV). On the other hand, the IP of toluene is higher than that of all the aromatic molecules except benzene as shown in Table 2. The toluene molecular ions react with analyte molecules via ion-neutral collisions. For most aromatic molecules, electron transfer will take place as shown in Scheme I, resulting in the formation of analyte radical molecular ions.

Scheme I

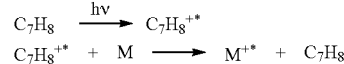

The energy deposition of Scheme I is determined by the IP differences between the analyte and toluene. For almost all aromatic molecules, the energy deposition is sufficiently low that analyte molecular ions are formed without fragmentation. This soft ionization is important for VR analyses due to the complexity of the sample compositions. Low levels of protonation have been observed for low molecular weight polar molecules. Protonation can be pronounced when more polar solvents (such as methanol and acetonitrile) are used.

Figure 11:
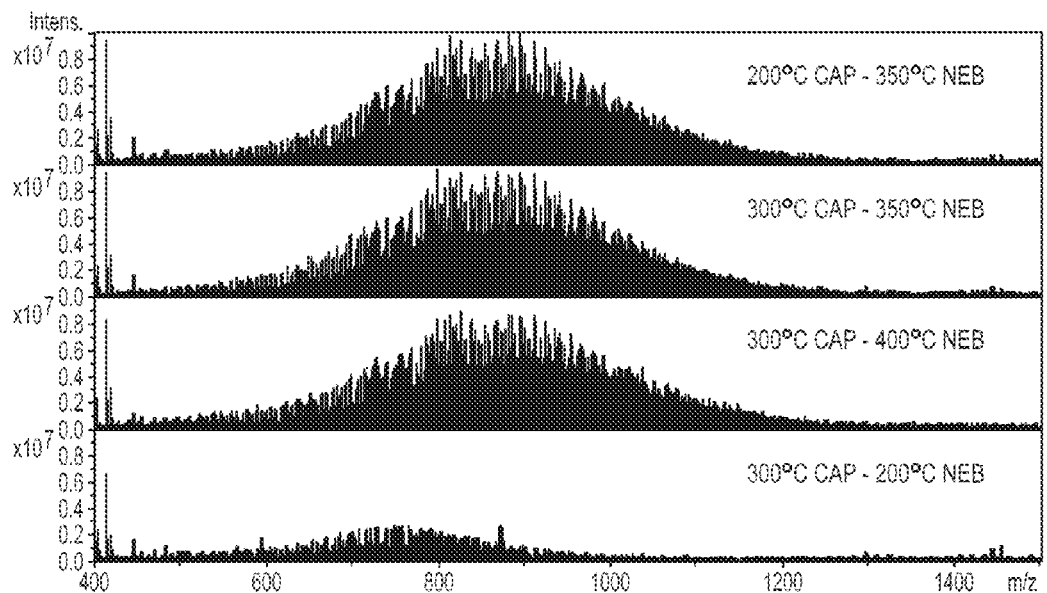
FIG. 11 shows the effect of nebulizer and capillary temperature.

Sample volatilization in APPI is a combined nebulizing and heating process. Nebulizing temperature has a large impact on the volatilization. Once ions are formed, they are transported into the source chamber for further manipulation via a heated capillary tube. FIG. 11 shows the temperature effects of APPI. An Arab Heavy distillate fraction (BP 1120-1305° F. (604-707° C.)) is analyzed by APPI-FTICR at different nebulizer (NEB) and capillary (CAP) temperatures. Mass spectra show a large increase in the higher mass intensity as nebulizing temperature is changed from 200° C. to 350° C. No change was found as the temperature was further increased to 400° C. The results suggest that 350° C. nebulizing temperature is sufficient to volatize and ionize molecules with BP up to 1300° F. MS signals show no difference between 200° C. and 300° C. capillary temperature, indicating that once ions are formed, re-condensation will not occur during the time period of our analysis.

Figure 12:
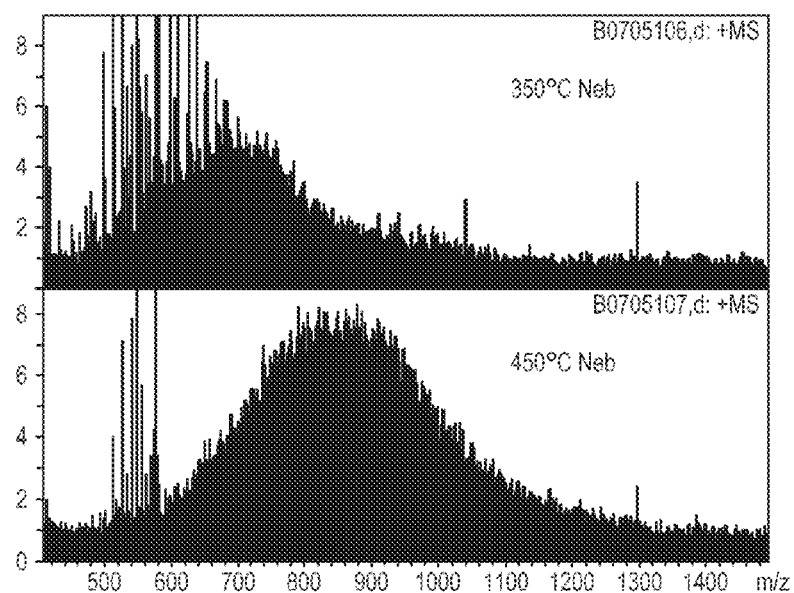
FIG. 12 shows APPI of asphatenes at 350 F and 450 F nebulizer temperatures.

When an n-heptane asphaltenes of Cold Lake VR (~50% of the material boils above 1380° F. (749° C.) based on high temperature simulated distillation) was subjected to the same tests, we notice the need for much higher NEB temperature. FIG. 12 compares the mass spectra of a VR asphaltenes between 350° C. and 450° C. NEB temperatures. Asphaltenes signals are barely visible at 350° C. and are very significant at 450° C. Since the maximum NEB temperature is 500° C., we have chosen 450° C. as our default operation temperature to avoid over heating the system and potential thermal decomposition.

Ionization of Polar Molecules by ESI

ESI has been widely explored for ionization of petroleum samples. It is also widely accepted that positive ion ESI (PESI) selectively ionizes basic nitrogen compounds via protonation while negative ion ESI (NEST) selectively ionizes acids, phenols and non-basic nitrogen compounds via de-protonation. In ESI, a large potential of approximately 2,000 to 4,000 V is applied to a capillary needle through which a sample solution containing electrolyte (e.g. formic acid for positive ion or $NH_4OH$ for negative ion) are introduced. A counter electrode is maintained at 0 V, thus creating a strong electric field between it and the capillary. The electric field permeates the solution at the capillary needle tip and causes separation of the ions in solution. In positive ion conditions, negative ions move toward the center of the capillary whereas positive ions are enriched at the surface of the liquid at the capillary tip. The repulsion of the excess charges at the surface and the pull of the electric field form a "Taylor cone" at the tip of capillary. As the charge repulsion overcomes the surface tension of the liquid, a fine spray of charged droplets is created. As those droplets pass through a heated capillary within the mass spectrometer, the solvent evaporates, increasing the surface charge density. Coulombic repulsion causes droplets to fission into successively smaller daughter droplets, resulting in the eventual removal of all solvent molecules to yield unhydrated gas-phase ions (charge residual model) or direct ejection of ions into gas phase (ion evaporation model).

Figure 13:
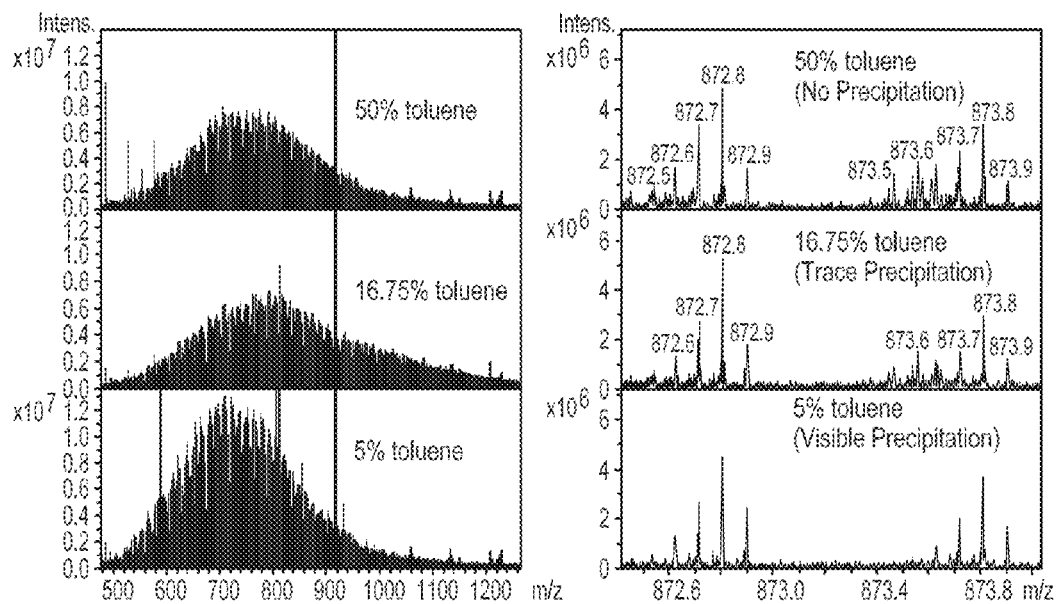
FIG. 13 shows solvent effect on ESI.

For ESI applications in petroleum, solvents are normally binary mixtures containing both petroleum-friendly solvent and ESI-friendly solvent, such as toluene/acetonitrile (positive ion mode) or toluene/methanol (negative ion mode). For VGO samples, toluene content can be as low as 5% without significant sample precipitation. For VR DAOs and asphaltenes, we have observed large solid precipitation using the conventional mix adopted for VGO analysis. All VR samples are soluble in 100% toluene. However, toluene does not spray under the ESI conditions. To obtain a steady ESI current, a maximal 50% toluene may be used. FIG. 13 showed the impact of toluene concentration on ESI responses of a Cold Lake VR DAO. As toluene concentration decreases, total ESI signal increases, particularly in the lower molecular weight region. The responses of the higher molecular weight species is decreasing. When we examine the detailed mass spectra (FIG. 13 (b)), it becomes clear that more condensed aromatic nitrogens were not detected in the case of 5% toluene, mostly likely due to the precipitation. 16.75% Toluene showed a broader mass distribution among the three. Despite minor precipitation of this solvent condition, the spectra showed overall better ESI performance. In our normal practice toluene concentration is normally controlled between 15 to 25%.

A uniform response factor is assumed for ESI although we realize there are significant variations in positive ion ESI responses for various nitrogen compound types[4]. In negative ion ESI of acids, the uniform response assumption is not far from reality. Previous research has shown that TAN measurements based on stearic acid match well with that of titration of total acids[5]. Similar to APPI applications, FTICR is mainly used to provide Z-distribution of homologues and heteroatom distribution of polar species in petroleum samples. The nitrogen concentrations are normalized to elemental nitrogen and acids are normalized to the TAN measurements. In our research, positive and negative ion ESI are used to detect bases and acids in VR. These molecules are used to construct basic nitrogen and acid compositions.

Figure 14:
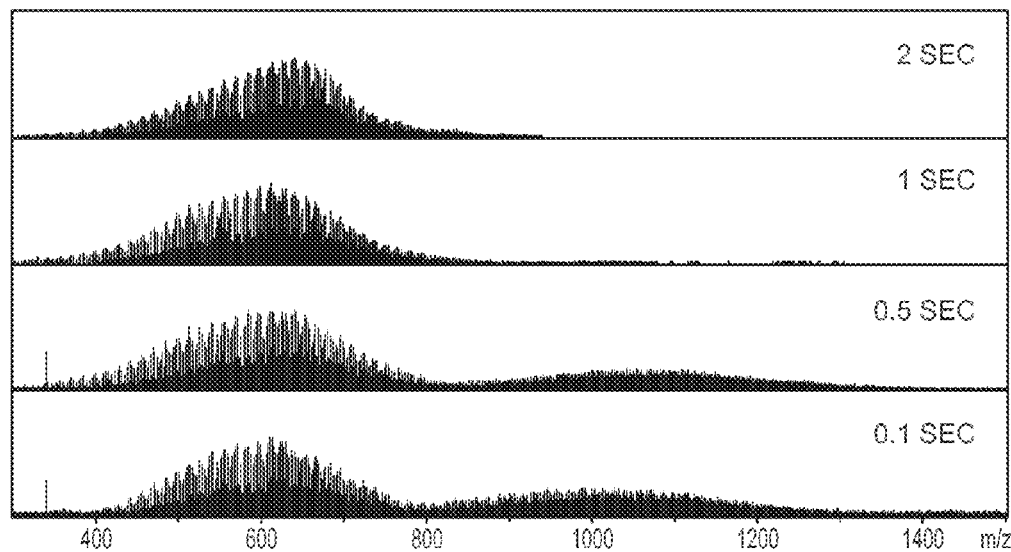
FIG. 14 shows the effect of accumulation time on dimers in ESI.

ESI is a soft ionization method which is also known to retain non-covalent structures in condensed phase. FIG. 14 shows an example of formation of non-covalent dimers and effect of ion accumulation on these dimers. The experiment is a positive ion ESI of a Arab heavy distillate (975-1120° F.). When accumulation time is very short (<0.5 Sec), the presence of dimer ions are evident. The increase of ion accumulation time in the hexapole ion trap provides sufficient ion-neutral collisions to disrupt the non-covalent interactions, even with very low ion kinetic energy (near thermal velocity). In normal ESI operations, ion accumulation time is typically maintained greater than 1 sec to reduce the probability of non-covalent interactions.

Compound Classes, Z Distribution, Total Carbon Number Distribution and Stoichiometry of Molecules FTICR MS provides three layers of chemical information for a petroleum system. The first level is heteroatomic classes (or compound classes), such as hydrocarbons (HC), 1 sulfur molecules (1S), 1 nitrogen molecules (1N), 2 oxygen molecules (2O), 1 nitrogen 1 oxygen molecules (1N1O), etc. The second level is Z-number distribution (or homologous series distribution). Z is defined as hydrogen deficiency as in general chemical formula, $C_cH_{2c+z}N_nS_sO_o$. The more negative the Z-number, the more unsaturated the molecules. Another commonly used term is called double bond equivalent (DBE). For a typical petroleum system, $DBE=1-(Z-n)/2$ where n is the number of nitrogen atoms. The third level of information is the total carbon number distribution or molecular weight distribution of each homologue. If compound core structure is known, total alkyl sidechain information can be derived by subtracting carbon number of cores.

Characterization of VR and Fractions

VRs are separated into eight fractions prior to MS characterization. These are saturates, 1, 2, 3, and 4+ ring aromatics, sulfides, polars and asphaltenes. Saturates are characterized by Field Desorption ionization coupled with a moderate resolution mass spectrometer. Positive and negative ion ESI-FTICR analyses of DAO are used to re-construct polar compositions.

Analyses of Aromatic Ring Class Fractions and Sulfides

APPI is used to ionize all aromatic ring class fractions and sulfide fraction. APPI-FTICR mass spectra of Cold Lake aromatic ring class fractions are shown in FIG. 3. M/z values of ARC 1 range from 450 to 1300 while that of ARC 4 range from 400 to 1200. Average MW decreases as ring class increases. This is mainly due to boiling point effects. For a given boiling point, more condensed aromatics have lower molecular weight. The fact that the upper mass of ARC4+ in FIG. 3 is lower than that of ARC 1, indicates some high molecular weight species in ARC4+ were not vaporized and ionized. A detailed view (3(b)) of m/z 688 shows a mass distribution shift toward the left side (more condensed), similar to that observed in VGO. Fewer components are observed in ARC 1 and 2, suggesting the effectiveness of the HPLC separation. Both ARC 3 and ARC 4+ contain a large number of peaks, indicating the complexity of these fractions. As ring class increases, H/C ratio decreases and S content increases.

Figure 15:
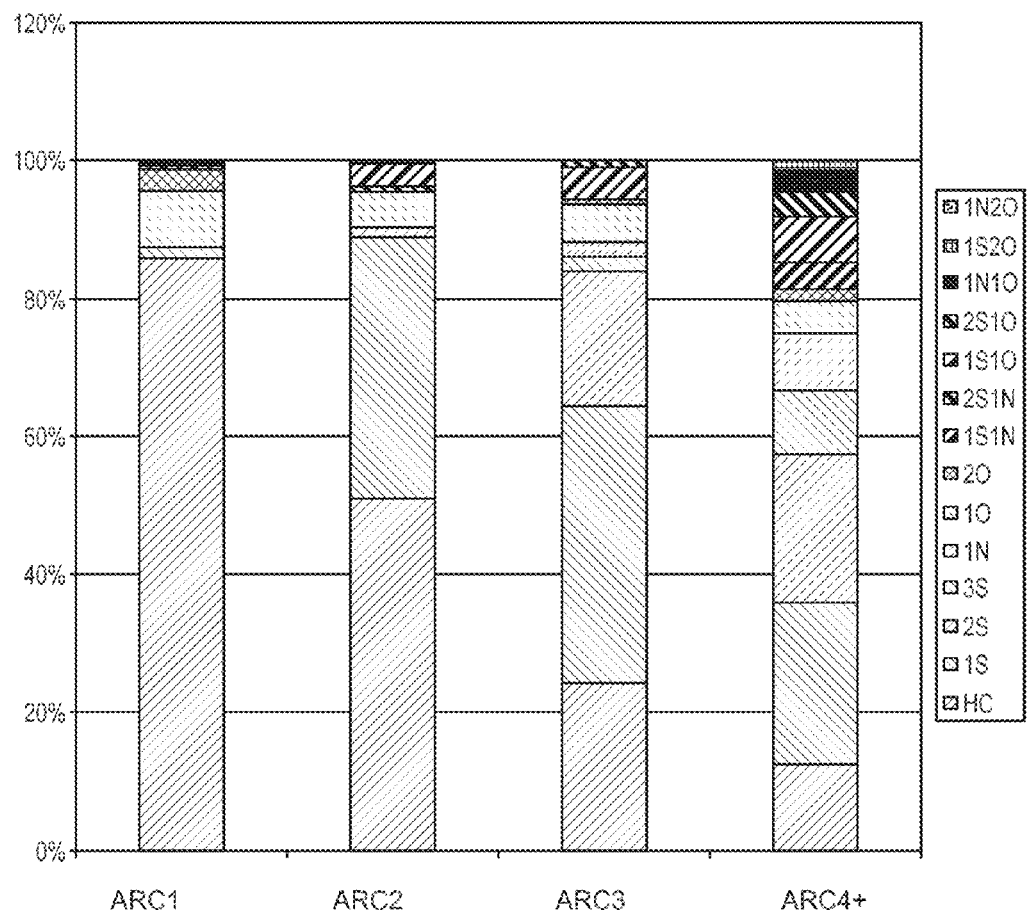
FIG. 15 shows the heteroatom classes of Cold Lake VR Aromatic Ring Class (ARC) fractions.

FIG. 15 shows the total compound classes observed by APPI-FTICR. The complexity of these fractions increase dramatically with ring class. Hydrocarbons are the major components of ARC 1. 1S, 2S and 3S contributions gradually increase as the ring class increases. Oxygenates were observed in all ARC fractions. Most oxygenates are 1O, 2O and 1S1O. In ARC 4+, 1N1O, 1S2O and 2S1O were also observed. 4-ring+ aromatic fraction contains up to 4 sulfur atoms per molecule. Sulfur incorporation clearly accompanied with aromatic ring growth. Substantial 1N and 1N1S molecules are observed in ARC4+. Nitrogen-containing molecules were detected in both ARC 3 and ARC 4+. Based on the nature of the chromatographic separation and our previous evaluation of VGO data, we believe that these nitrogen compounds are mostly non-basic nitrogens.

Figure 16:
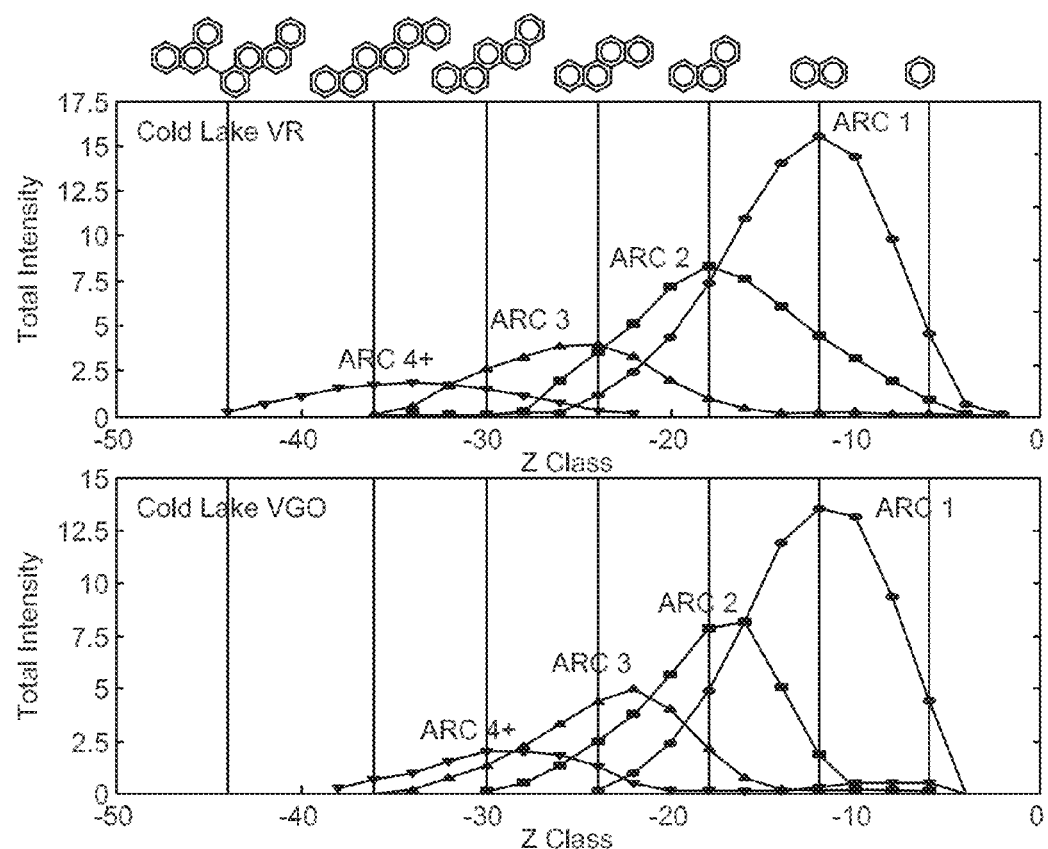
FIG. 16 shows a comparison of HC Z-number distribution between VR and VGO.

One of the most important data that FTICR-MS can provide to heavy hydrocarbon model-of-composition is the Z-number distribution. Z numbers can be used to construct molecules with additional input from NMR. FIG. 16 and compare the differences in Z distribution between VR and VGO of Cold Lake crude for HC class. A set of benchmarking aromatic structures were drawn to illustrate degrees of unsaturations. In the case of hydrocarbons (FIG. 16), the Z-distributions of ARC 1 and ARC 2 are very similar despite large differences in their MW distributions. The results suggest that hydrocarbon cores in ARC1 and ARC2 are probably similar between VGO and VR. Starting from ARC 3, the Z distribution of VR is becoming more negative. Even more striking differences in Z distribution were observed for ARC 4+ where VR Z values are much more negative than that of VGO.

Figure 17:
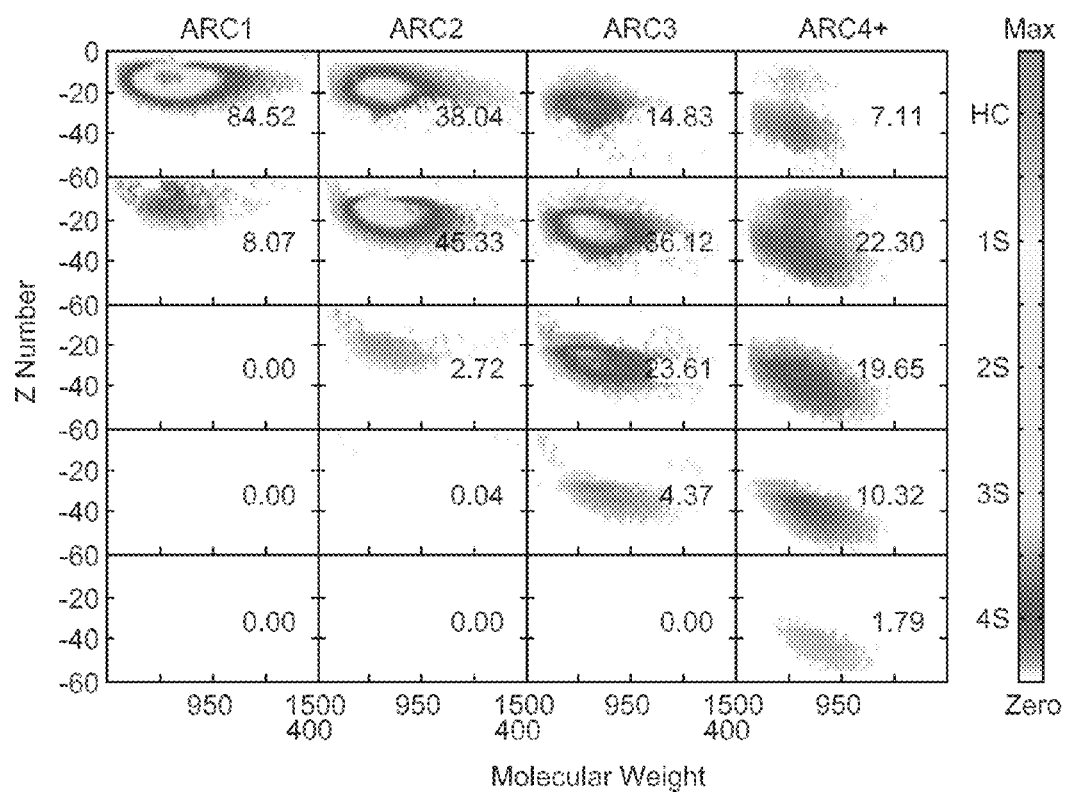
FIG. 17 shows Z-number and molecular weight distributions in Cold Lake aromatic ring fractions.

FIG. 17 shows image plots of ARC1-4+ compositions (HC, 1-4S). X-axis is the molecular weight (MW). Y-axis is the Z-number. Abundances of molecules are represented by the color scheme. Again, from ARC1 to ARC4+, the complexity and number of molecules increases. For example, ARC1, 2, 3, 4+ contains 3460, 6238, 7661 and 9988 unique molecules (excluding $^{13}C$ and $^{34}S$ isotopes). Molecular weight growth in ARC 1 and 2 are primarily governed by $CH_2$ extension. While ARC3 and ARC4+ show notable influence of Z-number on molecular weight, indicating aromatic ring growth contributed to the size or molecular weight of the molecules.

Figure 18:
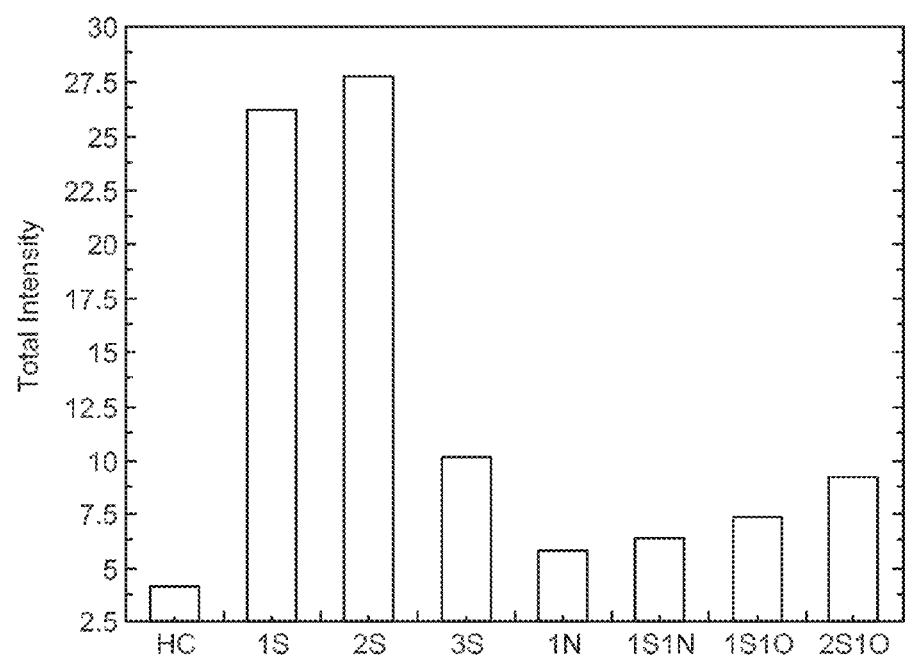
FIG. 18 shows the summary of sulfide species in Cold Lake.
Figure 19:
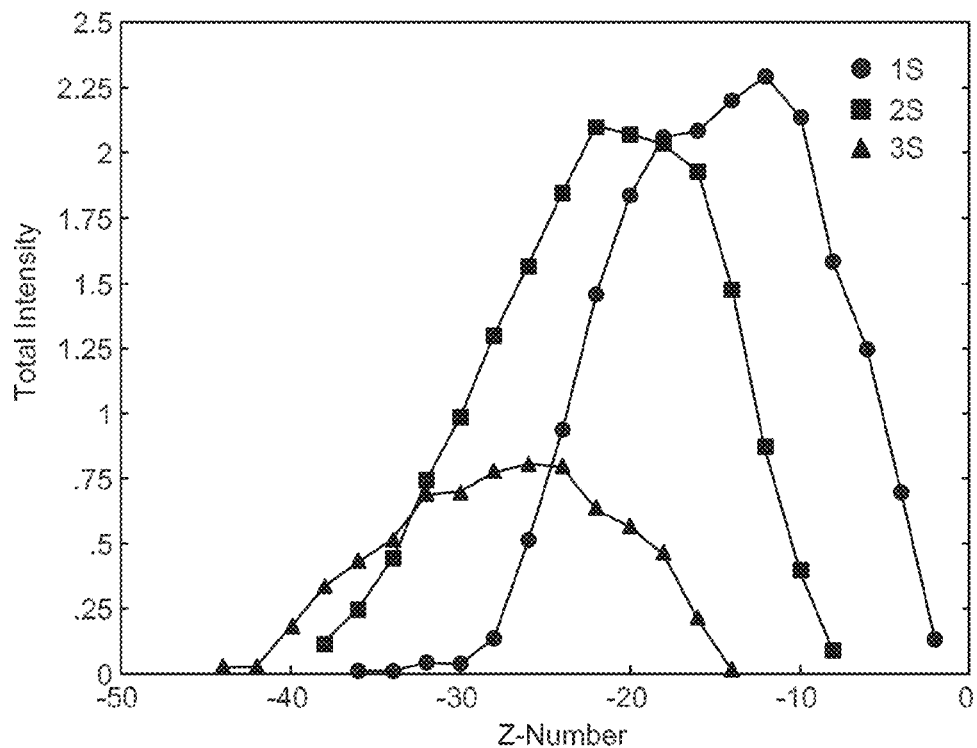
FIG. 19 shows Z-number distribution of sulfide molecules.

FIG. 18 and FIG. 19 show sulfide compound classes and Z-number distribution. As expected. Sulfur containing species are predominant. The Z-number distribution covers a wide range, indicating the presence of polyaromatic sulfides.

Analysis of Polar Molecules

Figure 20:
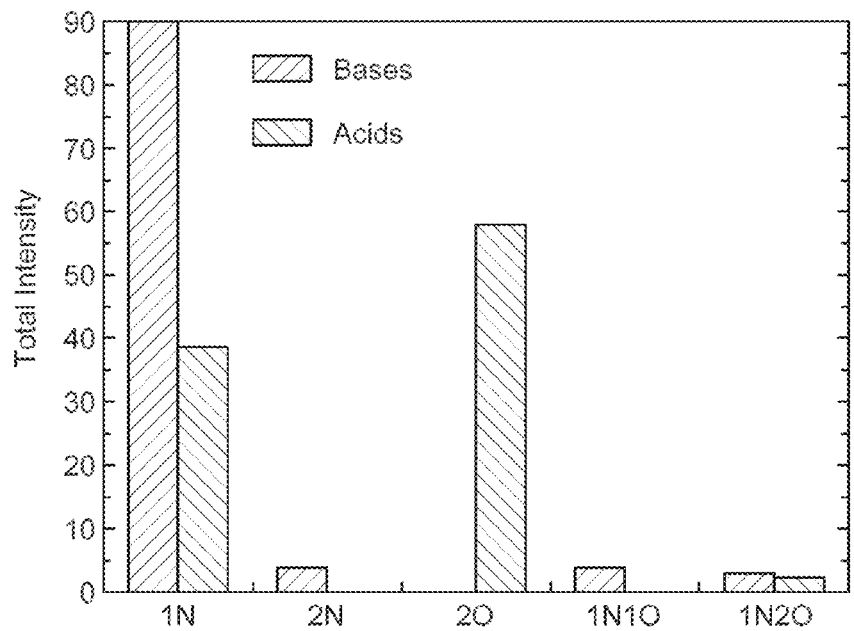
FIG. 20 shows the VR basic and acidic compound classes.
Figure 21:
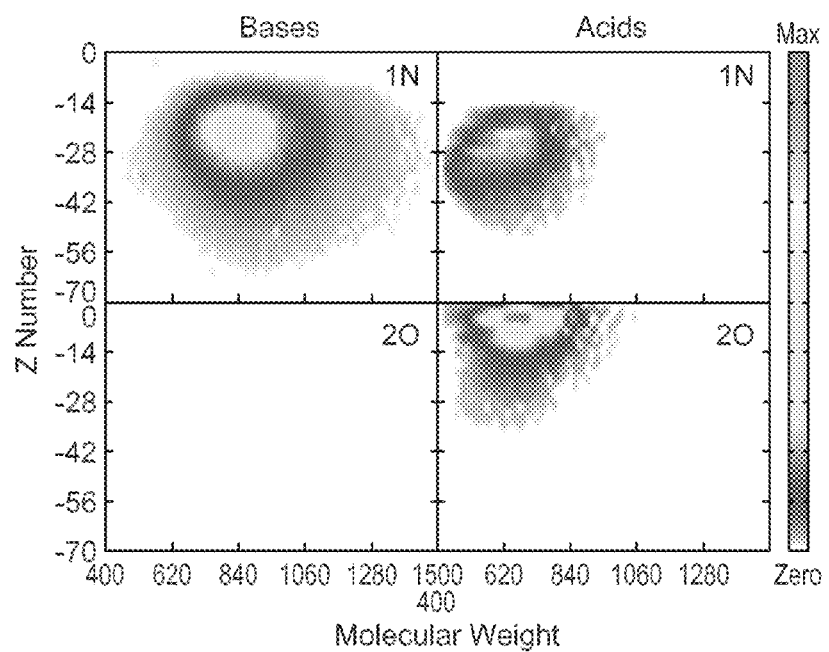
FIG. 21 shows Z-number and molecular weight distributions of bases and acids in DOBA VR.

Basic nitrogens in DAO are measured by positive ion ESI. Neutral nitrogens and acids were measured by negative ion ESI. FIG. 20 shows basic and acidic compound classes in DOBA VR. Doba is a low sulfur crude and therefore 1N species predominate the class distribution. High sulfur VR can contain substantial amounts of 1N1S, 1N2S and 2N species. Image plot is shown in FIG. 21. An examination of Z-number distribution of basic 1N class revealed the presence of 1 ring to 11 ring basic nitrogen aromatic compounds. Doba VR shows a high level of acids. Since VR has experienced thermal stress during vacuum distillation, It is expected that some acids were destroyed by the thermal process. The Z-distribution of acids shows the most abundant core structures are dicyclics. Z number up to −32 has been observed, suggesting the presence of up to 4 ring aromatic structures. The Z distribution of neutral nitrogens shows aromatic ring number ranges from 3 to 10.

Analysis of Asphaltenes

Figure 22:
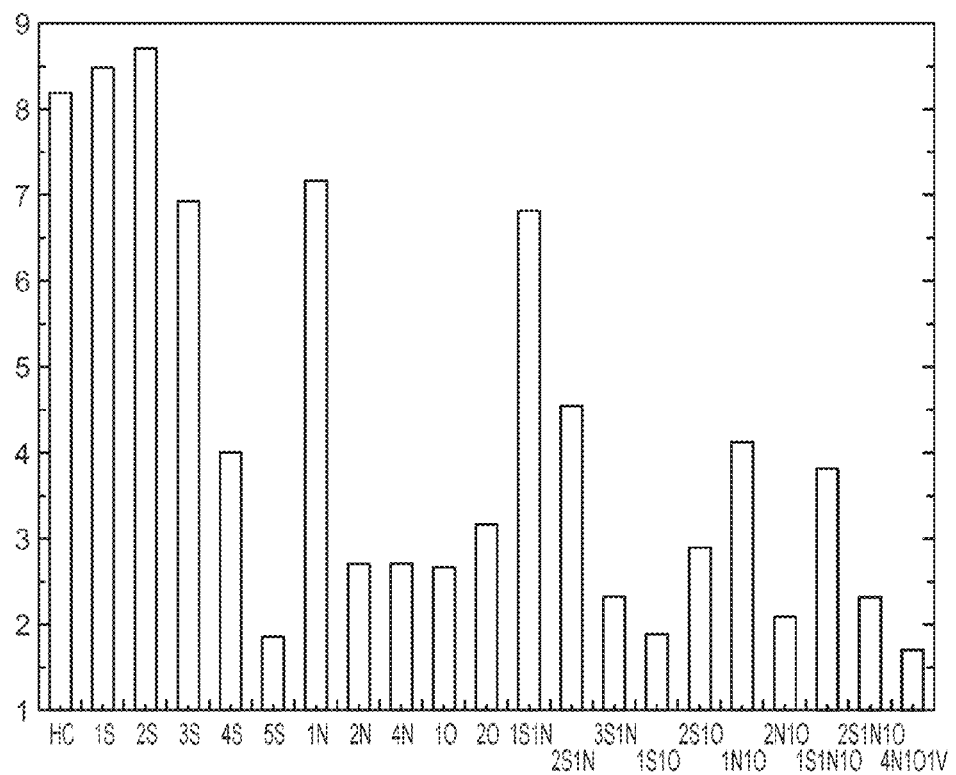
FIG. 22 shows compound classes in Cold Lake VR asphaltenes.
Figure 23:
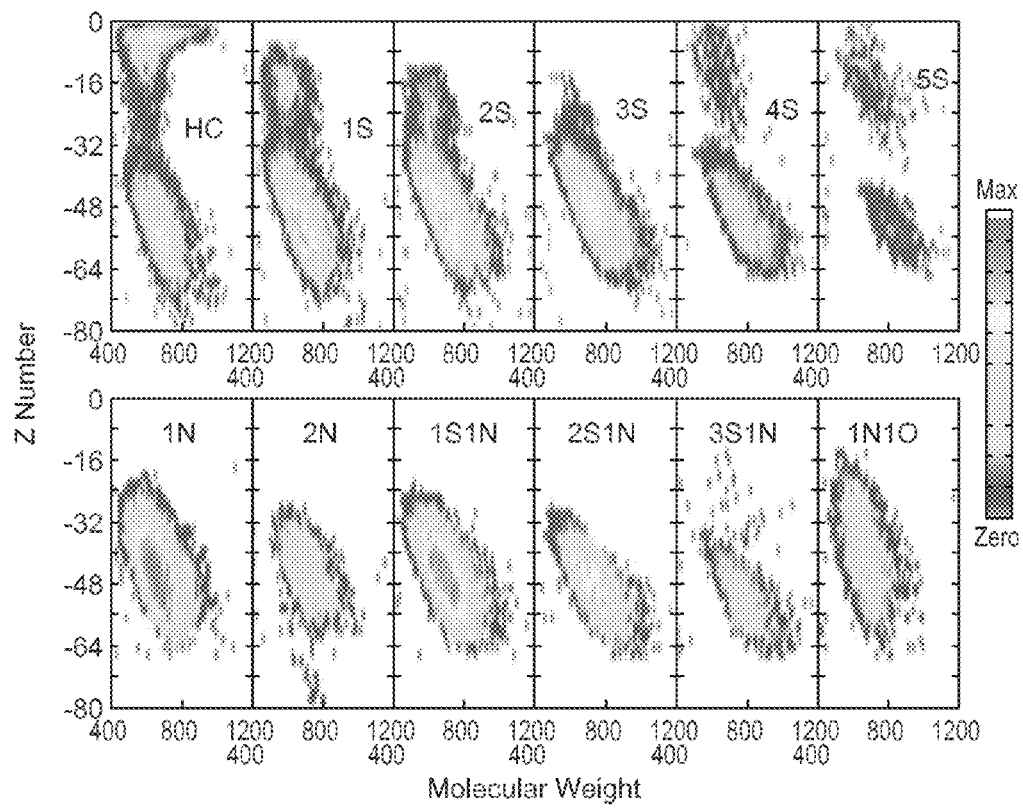
FIG. 23 shows Z-number and molecular weight distribution of Cold Lake asphaltene molecules.

A substantial amount of asphaltenes will boil above 1300° F. and may not be ionized by APPI. Alternative ionization methods, such as, MALDI and LDI, are helpful to determine those not seen by APPI. The compound classes in asphaltenes (FIG. 22) are extremely complicated. The most striking feature is that there is not one dominating class. Pure hydrocarbons are present in a small amount. 1S to 4S molecules were detected at abundant levels. 1N, 1N1S, 1N2S and 1N3S molecules were also observed. The total number of molecules (excluding $^{13}C$ and $^{34}S$ isotopes) in asphaltenes is about 200,000, 10 times higher than that in ARC4+. Image plot (FIG. 23) reveals strong influence of Z-number on molecular weight, indicating asphaltenes molecular weight growth is primarily driven by polyaromatic ring growth. Z-number distributions of asphaltenes molecules are extremely broad (from Z=−6 to −80) and centered around Z=−40 (six ring aromatics). HC class shows a bimodal Z-number distribution. Some of the Z>−18 molecules are clearly not n-heptane insolubles. These molecules are co-precipitated during the deasphalting process.

On-Line Chromatography-Mass Spectrometry

Figure 24:
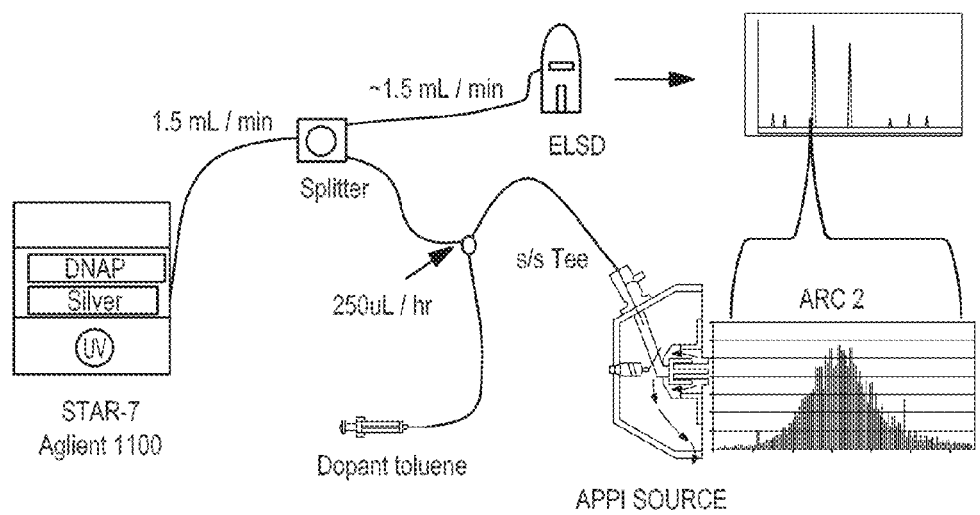
FIG. 24 shows an example of on-line chromatography mass spectrometry configuration. ELSD: Evaporative Light Scattering Detector
Figure 25:
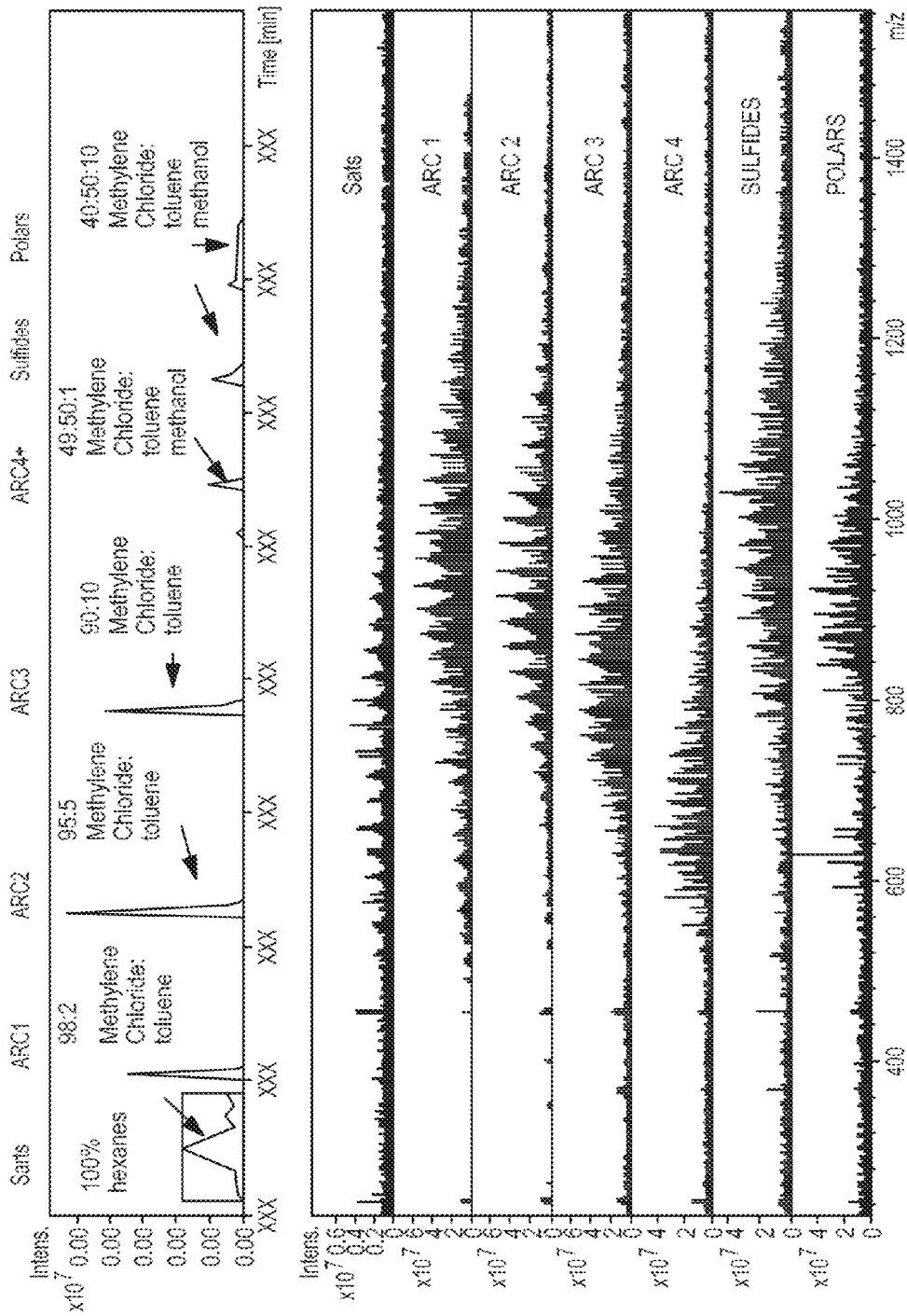
FIG. 25 shows HPLC-FTICR-MS Chromatogram and Average Mass Spectra
Figure 26:
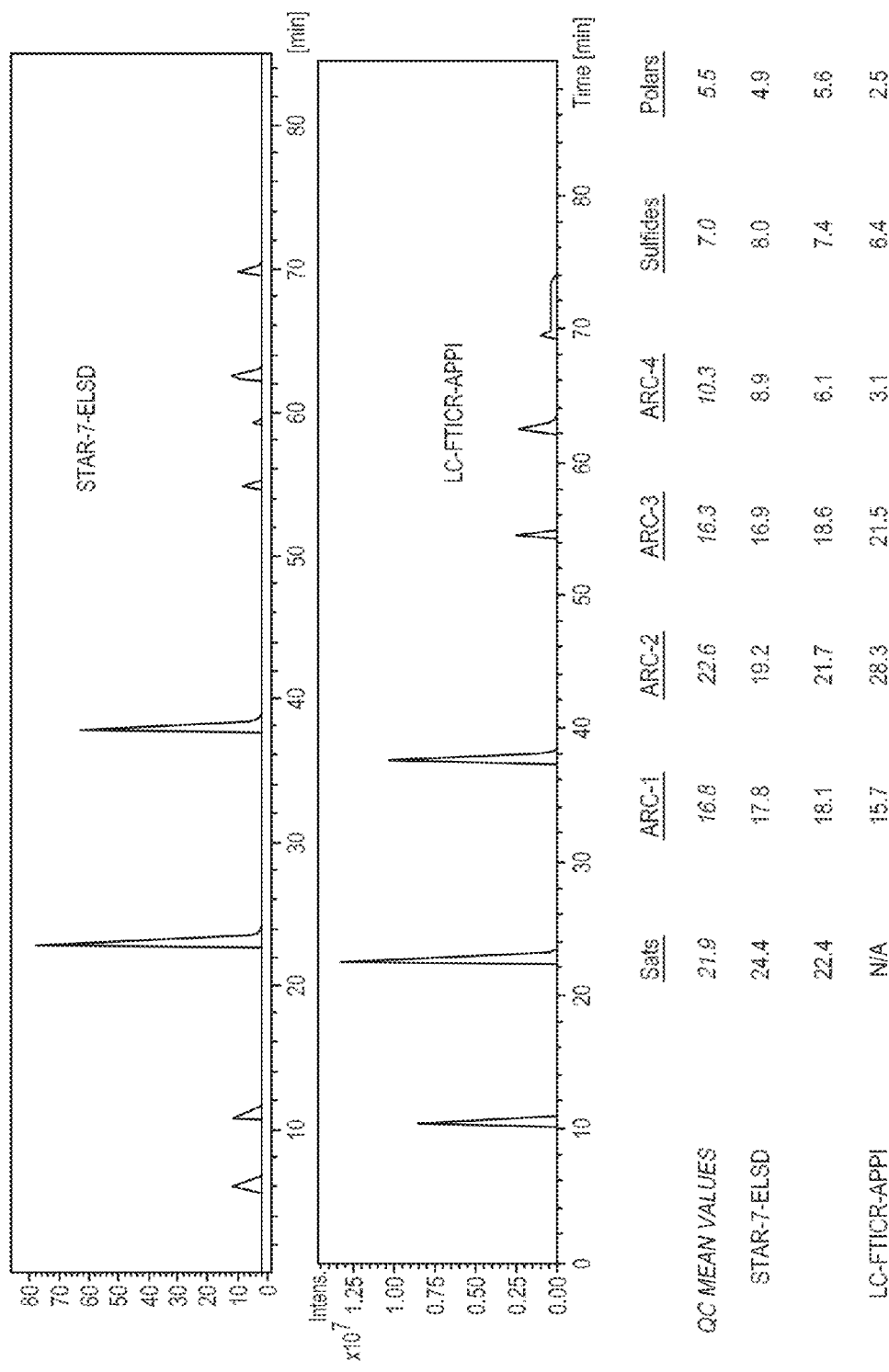
FIG. 26 shows Comparison of Results from HPLC-ELSD and HPLC-FTICR MS Using APPI

Analyses can be conducted using on-line chromatography mass spectrometry. By definition, on-line separation means that separated fractions are not physically collected after separation but directly transferred and analyzed by mass spectrometer. On-line chromatography mass spectrometry made the analysis more efficient in cost and time. We demonstrated the feasibility by coupling an HPLC system with FTICR-MS using APPI. FIG. 24 shows an example of the configuration. Liquid eluting from HPLC is divided into two streams by a splitter. Most liquid goes to the light scattering detector (ELSD). A small portion is infused directly into the APPI source of the FTICR-MS. Both chromatograms are recorded. The total ion chromatogram of a VGO sample is shown in FIG. 25 (top). An example of solvent program is given in the chromatogram. The sample are separated into saturate, ARC1-4+, sulfides and polars by HPLC. The effluents are directly ionized by APPI and mass analyzed by FTICR-MS. The average mass spectra of the eluted fractions are given in FIG. 25 (bottom). Quantification of the 7 lumps can be done by peak area integration. FIG. 26 compares the chromatograms from ELSD and APPI-FTICR MS. The chromatograms look very similar. The peak areas of the 7 lumps are also very similar. APPI cannot ionize saturate petroleum molecules.

CONCLUSIONS

We have developed FTICR-MS methods to characterize VR and isolated fractions. FTICR-MS provides heteroatom class distribution and Z-distribution that can be used to construct model-of-composition for heavy hydrocarbons, in conjunction with the MW distribution by FDMS, aromatic carbon content by NMR, S and N content by elemental, XPS and XANES analyses. Atmospheric pressure photoionization (APPI) using toluene as a solvent was identified to be the most effective ionization method for aromatic fractions, sulfides and asphaltenes. High vaporizing temperature (450° C.) assisted with nebulizing gases enables volatilization of molecules with boiling points as high as 1300° F. Electrospray ionization (ESI) is found to be the method of choice for polar molecules. At present, saturate hydrocarbons were analyzed by field desorption (FD) combined with a moderate mass resolution (~5000) mass spectrometer. FDMS is also used to provide molecular weight distributions for all VR fractions.

In analysis of VR, FTICR-MS provides composition of petroleum in terms of hydrogen deficiency (Z), heteroatom content (SNO) and total carbon number distribution. The detailed fractionation helps to narrow Z distributions of VR and significantly enhances the dynamic range of FTICR-MS. The ultra-high resolution enabled us to resolve mass overlaps and determine stoichiometry of molecules accurately. On average, we have detected about 3,000-200,000 species per fraction. A total of 300,000 molecules per VR have been resolved and measured in terms of specific elemental formulae. Z values as high as −80 have been detected, corresponding to structures containing 12 aromatic rings. The combination of APPI and ESI-FTICR and FDMS generated highly detailed composition of VRs that can be further reconciled with other analytical data.

REFERENCES

1. Qian, K.; Edwards, K. E.; Mennito, A. S.; Ferrughelli, D. T., Observation of Vanadyl Porphyrins and Sulfur-Containing Vanadyl Porphyrins in a Petroleum Asphaltene by Atmospheric Pressure Photon Ionization Fourier Transform Ion Cyclotron Resonance Mass Spectrometry. *Rapid Commun. Mass Spectrom.* 2008, 22, (14), 2153-2160
2. Chawla, Birbal; Green, Larry A. HPLC separation and quantitation of heavy petroleum fractions. PCT Int. Appl. (2010), 41 pp. CODEN: PIXXD2 WO 2010114587 A1 20101007 CAN 153:485056 AN 2010:1252505
3. Chawla, Birbal; Green, Larry A. Multi-dimensional HPLC separation technique (star7) for quantitative determinations of 7 fractions in heavy petroleum streams boiling above 550 F. U.S. Pat. Appl. Publ. (2010), 21 pp. CODEN: USXXCO US 2010218585 A1 20100902 CAN 153:363112 AN 2010:1103985
4. Qian, K. E., Edwards, Kathleen E.; Diehl, John H.; Green, Larry A., Fundamentals and Applications of Electrospray Ionization Mass Spectrometry for Petroleum Characterization. *Energy & Fuels* 2004, 18, (6), 1784-1791.
5. Qian, Kuangnan; Edwards, Kathleen E.; Dechert, Gary J.; Jaffe, Stephen B.; Green, Larry A.; Olmstead, William N. Distributed total acid number in petroleum and petroleum fractions by electrospray mass spectrometry. U.S. Pat. Appl. Publ. (2007), 20 pp. CODEN: USXXCO US 2007037288 A1 20070215 CAN 146:232304 AN 2007:175588

TABLE 1

Common mass overlaps

| Common Doublets | Mass Difference (mDa) | Resolution Needed at m/z 800 |
|---|---|---|
| $^{12}C \sim H_{12}$ | 93.4 | 8,565 |
| $^{32}S \sim C_2H_8$ | 90.1 | 8,879 |
| $^{16}O \sim CH_4$ | 36.0 | 22,222 |
| $^{13}CH \sim ^{14}N$ | 8.2 | 97,561 |
| $^{32}SH_4 \sim C_3$ | 3.4 | 235,294 |

TABLE 2

Ionization potentials of hydrocarbon molecules

| Compounds | IP (eV) |
|---|---|
| Hexane | 10.1 |
| Cyclohexane | 9.9 |
| Decane | 9.7 |
| n-Butyl cyclohexane | 9.6 |
| Decalin | 9.4 |
| Benzene | 9.2 |
| Toluene | 8.8 |
| n-Butyl benzene | 8.7 |
| Indane | 8.6 |
| Naphthalene | 8.1 |
| Benzothiophene | 8.1 |
| Dibenzothiophene | 8.0 |
| Phenanthrene | 7.9 |
| n-Butyl naphthalene | 7.8 |
| Chrysene | 7.6 |

APPENDIX II

Molecular Formula Distributions of Vacuum Resid Reconciled to the HHMoC Research Analytical Protocol An algorithm that computes the weight percent distributions of molecular formulae within vacuum residuum (VR, or resid) is disclosed in this Appendix. These molecular formula distributions are reconciled to the heavy hydrocarbon model of composition (HHMoC) Research Analytical Protocol (see below). This reconciliation is a critical step in the assignment of a molecular lump library to resid fractions, and subsequent delivery to composition-based resid upgrading models.

In the reconciliation algorithm, the FTICR-MS data are blended by fraction weight, then autotuned to satisfy property constraints. These property constraints are taken from the HHMoC research analytical protocol. They include: fraction weight, and weight percent of hydrogen, sulfur, nitrogen, nickel and vanadium in HHMoC fractions with available data.

HHMoC Research Analytical Protocol

In the HHMoC research analytical protocol (see schematic in FIG. 9), n-heptane separates a resid sample into de-asphalted oil (DAO), and asphaltene fractions. Next, a high-performance liquid-chromatographic (LC) technique separates the DAO into saturates, ARC1-4, sulfides, and polars. These seven DAO fractions, and the asphaltene fraction, are analyzed by a variety of methods. In each HHMoC fraction except DAO saturates and polars, ultrahigh resolution Atmospheric-pressure Photoionization Fourier Transform Ion Cyclotron Resonance mass spectrometry (APPI-FTICR-MS) measures the molecular formula distribution. A VR molecule's molecular formula is given by $$C_c H_{2c+Z} S_s N_n O_o Ni_{ni} V_v \quad (1)$$

Here, a molecule's carbon number is c, its hydrogen deficiency class Z, and s, n, o, are the stoichiometric coefficients of sulfur, nitrogen and oxygen, respectively. APPI-FTICR-MS has also detected organometallic compounds within selected VR fractions. These organometallic (porphyrin) compounds contain one atom each of either nickel, or vanadium [4]. In the molecular formula (1), the stoichiometric coefficients of nickel, and of vanadium, are ni, v, respectively.

In lieu of Eqn. (1), we report the molecular formulae of a molecule derived from FTICR-MS analysis as a triplet of three attributes: the molecule's nominal mass, MW (g/mol), its hydrogen deficiency class, Z, and its molecular type, T. The molecular type T takes a naming convention that includes the number of heteroatoms (s,n,o), and metal atoms (ni,v) in a resid molecule (see Table 2). This reporting convention is equivalent to Eqn. (1); the carbon number c of a molecule can be uniquely determined because a molecule's nominal mass equals the sum of the nominal mass in each atom type within the said molecule, where the nominal mass in each atom type equals its known atomic mass (C=12, H=1, S=32, N=14, Ni=59, V=51) multiplied by the number of atoms of that type (c,2c+Z, s,n,ni,v). From this atomic mass balance, the carbon number, c reads:

$$c = (MW - (Z + 32s + 14n + 16o + 59ni + 51v))/14 \quad (2)$$

Negative- and positive-ion electrospray (NEST- and PESI-) FTICR-MS is performed on the DAO fraction to detect heteroatom-rich molecules that elute in a variety of LC fractions. NESI-FTICR-MS can detect non-basic nitrogen and acids; PESI-FTICR-MS detects primarily basic nitrogen compounds. At present, the distribution of molecules comprising the DAO polar fraction is assumed to be the superposition of the NESI- and PESI-FTICR-MS spectra; APPI-FTICR-MS spectra of selected DAO polar fractions have been obtained on a non-routine basis, but are not reported here.

Reconciliation Algorithm

Inputs to the reconciliation algorithm, and computations performed in the algorithm are detailed below.

a) Inputs

Inputs to the reconciliation algorithm are taken from the HHMoC research analytical protocol (see FIG. 1). Mass-spectrometry (MS) inputs include: APPI-FTICR-MS analysis of the DAO ARC1-4, DAO sulfides, and asphaltene fractions, NESI/PESI-FTICR-MS analysis of the DAO. As mentioned above, superposition of the NESI- and PESI-FTICR-MS analysis of the DAO is used to synthesize an FTICR-MS analysis of the DAO polars fraction. APPI-FTICR-MS analysis of this polars fraction has been conducted on a number of samples in the current HHMoC VR library, but not on a routine basis. Weights on a 100% resid basis of each HHMoC fraction are obtained by material balance of the de-asphalting and DAO LC separation steps.

Elemental properties of selected HHMoC fractions used as inputs include: hydrogen, sulfur, nitrogen, nickel and vanadium content. Hydrogen contents of asphaltenes and of the following DAO fractions are measured by combustion (ASTM D 5291): saturates, aromatics, sulfides, and polars. Nitrogen content of asphaltenes, and the aromatics, sulfides, and polar fractions of the DAO are also measured using the ASTM D 5291 technique. At present, the sulfur content of all HHMoC fractions, except DAO saturates, are measured by ASTM D 2622 X-ray fluorescence. Nickel and vanadium content, among other metals, is typically measured on the total resid, asphaltene, and DAO fractions using the ASTM D 5708 technique.

b) Computational Details

In the new reconciliation algorithm, we compute the molecular formula distribution of molecules that are made consistent with the HHMoC research analytical protocol (see above). This distribution is expressed mathematically as wt % abundance of molecular lumps, as is done in SOL modeling applications. Unlike SOL, the description of a molecular lump in this work takes only sufficient information to identify its HHMoC fraction, and its molecular formula per the three-attribute convention detailed in Section 2. Thus, the weight percent abundance (100 wt % resid basis) of a molecular lump in this work is expressed as $w(f,MW,Z,T)$. The HHMoC fraction index takes positive integers, $f=1, 2, 3, \ldots 11$ and is defined in Table 3.

TABLE 3

HHMoC Fraction Indices

| Fraction | Index, f |
|---|---|
| DAO saturates | 1 |
| DAO ARC1 | 2 |
| DAO ARC2 | 3 |
| DAO ARC3 | 4 |
| DAO ARC4 | 5 |
| DAO sulfides | 6 |
| DAO polars | 7 |
| asphaltenes | 8 |
| DAO aromatics | 9 |

TABLE 3-continued

HHMoC Fraction Indices

| Fraction | Index, f |
|---|---|
| DAO | 10 |
| resid | 11 |

Molecular types, T, depend on the stoichiometric coefficients of heteroatoms, s, n, o and of metals ni, v. To date, a total of 35 molecular types appear in HHMoC applications (see Table 4).

TABLE 4

Heteroatom Stoichiometric Coefficients of Molecular Types in HHMoC Applications

| Type, T | Stoichiometric coefficients | | | | |
|---|---|---|---|---|---|
| | s | n | o | ni | v |
| HC | 0 | 0 | 0 | 0 | 0 |
| 1S | 1 | 0 | 0 | 0 | 0 |
| 2S | 2 | 0 | 0 | 0 | 0 |
| 3S | 3 | 0 | 0 | 0 | 0 |
| 1N | 0 | 1 | 0 | 0 | 0 |
| 1S1N | 1 | 1 | 0 | 0 | 0 |
| 1O | 0 | 0 | 1 | 0 | 0 |
| 1N2O | 0 | 1 | 2 | 0 | 0 |
| 4N1O1V | 0 | 4 | 1 | 0 | 1 |
| 1S1O | 1 | 0 | 1 | 0 | 0 |
| 1S1N1O | 1 | 1 | 1 | 0 | 0 |
| 2S1O | 2 | 0 | 1 | 0 | 0 |
| 2S1N | 2 | 1 | 0 | 0 | 0 |
| 2S1N1O | 2 | 1 | 1 | 0 | 0 |
| 4S | 4 | 0 | 0 | 0 | 0 |
| 5S | 5 | 0 | 0 | 0 | 0 |
| 3N | 0 | 3 | 0 | 0 | 0 |
| 4N | 0 | 4 | 0 | 0 | 0 |
| 1S2N | 1 | 2 | 0 | 0 | 0 |
| 1S4N | 1 | 4 | 0 | 0 | 0 |
| 3S1O | 3 | 0 | 1 | 0 | 0 |
| 3S1N | 3 | 1 | 0 | 0 | 0 |
| 3S1N1O | 3 | 1 | 1 | 0 | 0 |
| 4S1N | 4 | 1 | 0 | 0 | 0 |
| 2O | 0 | 0 | 2 | 0 | 0 |
| 4O | 0 | 0 | 4 | 0 | 0 |
| 1N1O | 0 | 1 | 1 | 0 | 0 |
| 1S4N1O1V | 1 | 4 | 1 | 0 | 1 |
| 2N | 0 | 2 | 0 | 0 | 0 |
| 2N1O | 0 | 2 | 1 | 0 | 0 |
| 3N1O | 0 | 3 | 1 | 0 | 0 |
| 1S2N1O | 1 | 2 | 1 | 0 | 0 |
| 1S2O | 1 | 0 | 2 | 0 | 0 |
| 4N1Ni | 0 | 4 | 0 | 1 | 0 |
| 1S4N1Ni | 1 | 4 | 0 | 1 | 0 |

Nominal molecular weight, MW, can take any positive integer. However, nominal molecular weights appearing in FTICR-MS spectra rarely exceed 3000 g/mol. Hydrogen deficiency class, Z takes integers $Z=2, 1, 0, \ldots -\infty$. For molecules that have even numbers of nitrogen atoms, i.e. the stoichiometric index $n=0, 2, 4, \ldots$, the hydrogen deficiency class Z and the nominal molecular weight MW are even integers. For molecules with odd numbers of nitrogen atoms, i.e. $n=1, 3, 5, \ldots$, hydrogen deficiency class Z and molecular weight MW are odd integers.

In first step of the reconciliation algorithm, a vector of initial molecular lump abundances $w^*(f,MW,Z,T)$ are set equal to the values measured by FTICR-MS analyses of selected HHMoC fractions $f=2, 3, \ldots 11$ (see Table 1). As noted in Section 3a, the initial molecular lump abundance in the DAO polars fraction $w^*(7,MW,Z,T)$ is synthesized by blending the NESI- and PESI-FTICR-MS analysis of the DAO fraction. In the DAO saturates fraction, the initial molecular lump abundances w*(1,MW,Z,T) made equal to that of its FDMS spectra, where the hydrogen deficiency classes Z are assumed to equal the nominal hydrogen deficiency class X. Next, the initial molecular lump abundances w*(f,MW,Z,T) are adjusted to reconciled values w(f,MW,Z,T). This adjustment is done such that the loss of information entropy is minimized, and such that the reconciled values w(f,MW,Z,T) satisfy a list of linear property constraints $$\sum_{i=1}^{N} a_{ji} w_i = b_j \quad (3)$$

for $j = 1, 2, \ldots, NP$

Here, $a_{ji}$ is the density of property j in molecular lump i, and $b_j$ is the measured value of property j. (see Table 3). Each molecular lump i is identified by its HHMoC fraction, f, and the three attributes MW, Z, and T. In the constrained optimization of information entropy, one solves the following Euler-Lagrange equation to determine a set of Lagrange multipliers $\lambda_k$:

$$\sum_{i=1}^{N} a_{ji} w_i^* \exp\left(-1 + \sum_{k=1}^{NP} \lambda_k a_{ki}\right) = b_j \exp(-\eta_j \lambda_j) \quad (4)$$

for $j = 1, \ldots, NP$

The softness parameters $\eta_j$ are zero to denote hard constraints. Otherwise, they are non-zero to facilitate convergence of the Euler-Lagrange Eqn. (4) when selected measured properties $b_j$ have significant uncertainty; non-zero values of these parameters are typically chosen by trial-and-error (see Table 5).

TABLE 5

Property Balance Constraints in HHMoC Autotuning Step

| Property value, b | Index of HHMoC fractions, f (see Table 1) | Non-zero values of property density, a | Softness parameter, η |
|---|---|---|---|
| Total weight (100 wt % resid basis) | All fractions, i.e. f = 1, 2, 3, ..., 11 | a = 1 for all molecules | 0 |
| Fraction wt %, total resid basis | All fractions except DAO saturates, i.e. f = 2, 3, 4, ..., 11 | a = 1 for all molecules in fraction f | 0 |
| Hydrogen wt % in fraction, total resid basis | All fractions, i.e. f = 1, 2, 3, ..., 11 | a = weight fraction hydrogen for all molecules in fraction f | 1.0E−06 |
| Sulfur wt % in fraction, total resid basis | All fractions except DAO saturates, i.e. f = 2, 3, 4, ..., 11 | a = weight fraction sulfur for all molecules in fraction f | 1.0E−06 |
| Nitrogen wt % in fraction, total resid basis | f = 6, 7, 8, 9 only | a = weight fraction nitrogen for all molecules in fraction f | 1.0E−06 |

TABLE 5-continued

Property Balance Constraints in HHMoC Autotuning Step

| Property value, b | Index of HHMoC fractions, f (see Table 1) | Non-zero values of property density, a | Softness parameter, η |
|---|---|---|---|
| Nickel wt % in fraction, total resid basis | f = 8, 10 if data available; f = 11 otherwise | a = weight fraction nitrogen for all molecules in fraction f | 0 |
| Vanadium wt % in fraction, total resid basis | f = 8, 10 if data available; f = 11 otherwise | a = weight fraction vanadium for all molecules in fraction f | 0 |

The vector of reconciled lump weights w(f,MW,Z,T) is determined by post-processing the solution of Eqn. (E-2):

$$w_i = w_i^* \exp\left(-1 + \sum_{j=1}^{NP} a_{ij} \lambda_j\right) \quad (4)$$

for $i = 1, \ldots, N$

The invention claimed is:

1. A method to determine the model-of-composition of a sample of petroleum resid comprising:
   (a) separating the resid sample into asphaltenes and deasphalted oils (DAO) and separating the deasphalted oils (DAO) into chemical meaningful classes including saturates, aromatics, sulfides and polars; wherein said aromatics are separated into aromatic ring class fractions including 1-ring aromatics (ARC1), 2-ring aromatics (ARC2), 3-ring aromatics (ARC3), 4-ring+ aromatics (ARC4+);
   (b) obtaining molecular ions or pseudo molecular ions of each of the asphaltenes, separated DAO and separated classes using a combination of Atmospheric Pressure Photoionization (APPI) or Atmospheric Pressure Chemical Ionization (APCI) and Field Desorption/Field Ionization and Electrospray Ionization (ESI) in high resolution mass spectrometry; wherein using ESI includes using positive ion electrospray ionization Fourier-transform ion cyclotron resonance mass spectrometry (PEST FTICR-MS) to ionize basic nitrogen molecules and by means of negative ion electrospray ionization Fourier-transform ion cyclotron resonance mass spectrometry (NEST FTICR-MS) to ionize acidic molecules;
   (c) determining elemental formula and assigning structure of said molecular ions or pseudo molecular ions and quantifying their corresponding concentrations in the asphaltenes, separated DAO and separated fractions from the high resolution mass spectrometry; and
   (d) combining compositions of separated fractions from act (c);
   (e) directly measuring bulk properties, average structures, and molecular weight distribution of the resid, asphaltenes and separated DAO and separated fractions;
   (f) minimally adjusting the molecular compositions obtained from acts (a)-(d) to match the properties the directly measured by act (e) to obtain a model-of-composition.

2. The method of claim 1, in which the resid separation and spectrometry analyses are performed by on-line chromatography-mass spectrometry.

3. The method of claim 1, in which the molecular ion or pseudo molecular ion structures remain intact after the ionization.

4. The method of claim 1 which includes the step of superimposing the PESI FTICR-MS and NESI FTICR-MS analyses.

5. The method of claim 1 in which the molecular weight of each separated classis matched to the molecular weight distribution of field-desorption ionization mass spectrometry (FDMS) analysis.

6. The method of claim 1 in which the ionization of molecules boiling above 1300° F. is by means of laser desorption ionization.

7. The method of claim 1 in which the ionization of molecules boiling above 1300° F. is by means of matrix assisted laser desorption.

8. The method of claim 1 in which the consolidation uses lumps to normalize concentrations.

9. The method of claim 1 in which the bulk properties include bulk elemental properties, which include hydrogen, sulfur, nitrogen, nickel and vanadium content.

10. The method of claim 9 in which the bulk properties include bulk composition and structural properties, which include:% Aromatic carbon (Ca), Average aromatic cluster size (C#), amount of C in long chains, degree of chain branching, organic forms of sulfur, pyrrolic, pyridinic and quaternary nitrogens.

11. The method of claim 10 in which the adjusting step uses molecular properties including Microcarbon Residue (MCR) or Conradson Carbon Residue (CCR) content, molecular weight distribution by FDMS and boiling point distribution by SIMDIS.

* * * * *